(12) United States Patent
Suddaby

(10) Patent No.: US 10,898,346 B1
(45) Date of Patent: Jan. 26, 2021

(54) EXPANDABLE INTERVERTEBRAL FUSION IMPLANT

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 0 days.

(21) Appl. No.: 16/516,416

(22) Filed: Jul. 19, 2019

(51) Int. Cl.
*A61F 2/44* (2006.01)
*A61F 2/30* (2006.01)

(52) U.S. Cl.
CPC ...... *A61F 2/447* (2013.01); *A61F 2002/3055* (2013.01); *A61F 2002/30261* (2013.01); *A61F 2002/30383* (2013.01); *A61F 2002/30405* (2013.01); *A61F 2002/30579* (2013.01); *A61F 2002/30622* (2013.01)

(58) Field of Classification Search
None
See application file for complete search history.

(56) References Cited

U.S. PATENT DOCUMENTS

| | | | |
|---|---|---|---|
| 5,483,463 A | 1/1996 | Qin et al. | |
| 5,505,732 A | 4/1996 | Michelson | |
| 5,653,761 A | 8/1997 | Pisharodi | |
| 5,653,762 A | 8/1997 | Pisharodi | |
| 5,665,122 A | 9/1997 | Kambin | |
| 5,683,463 A | 11/1997 | Godefroy et al. | |
| 6,126,660 A | 10/2000 | Dietz | |
| 6,159,244 A | 12/2000 | Suddaby | |
| 6,174,334 B1 | 1/2001 | Suddaby | |
| 6,325,827 B1 | 12/2001 | Lin | |
| 6,332,895 B1 | 12/2001 | Suddaby | |
| 7,044,971 B2 | 5/2006 | Suddaby | |
| 8,491,659 B2 | 7/2013 | Weiman | |
| 8,632,593 B2 | 1/2014 | Suh et al. | |
| 8,845,731 B2 | 9/2014 | Weiman | |
| 8,845,732 B2 | 9/2014 | Weiman | |
| 8,852,279 B2 | 10/2014 | Weiman | |
| 9,155,628 B2 | 10/2015 | Glerum et al. | |
| 9,833,337 B2 | 12/2017 | Hleihil et al. | |
| 9,949,841 B2 | 4/2018 | Glerum et al. | |
| 10,010,429 B2 | 7/2018 | Dmuschewski | |
| 10,085,849 B2 | 10/2018 | Weiman et al. | |
| 10,117,753 B2 | 11/2018 | Suh et al. | |
| 10,137,001 B2 | 11/2018 | Weiman | |
| 10,143,566 B2 | 12/2018 | Hyder | |
| 10,154,912 B2 | 12/2018 | Glerum | |

(Continued)

FOREIGN PATENT DOCUMENTS

WO    WO2009/064787    5/2009

*Primary Examiner* — Sameh R Boles
(74) *Attorney, Agent, or Firm* — Simpson & Simpson, PLLC; Michael Nicholas Vranjes

(57) ABSTRACT

An expandable intervertebral fusion implant capable of being expanded in three dimensions, said implant including an inferior component, including a plate, and a first wedge slidably connected to the plate, the first wedge having a first surface, and a superior component including a second wedge, the second wedge having a second surface, wherein the first surface is operatively arranged to engage the second surface to displace the superior component relative to the inferior component. The surfaces of the wedges may be angled and include a plurality of corrugations or steps which engage to allow the implant to expand and collapse.

28 Claims, 14 Drawing Sheets

(56) References Cited

U.S. PATENT DOCUMENTS

| | | |
|---|---|---|
| 2005/0256576 A1 | 11/2005 | Moskowitz et al. |
| 2008/0140207 A1* | 6/2008 | Olmos .................. A61F 2/4657 623/17.16 |
| 2009/0222100 A1* | 9/2009 | Cipoletti ............... A61F 2/4611 623/17.16 |
| 2013/0190876 A1 | 7/2013 | Drochner et al. |
| 2015/0073552 A1* | 3/2015 | To ......................... A61F 2/4611 623/17.15 |
| 2016/0025629 A1 | 1/2016 | Kettler et al. |
| 2016/0256291 A1* | 9/2016 | Miller ................... A61F 2/4611 |
| 2018/0078384 A1 | 3/2018 | Suddaby |
| 2018/0193164 A1* | 7/2018 | Shoshtaev ............. A61F 2/4425 |
| 2018/0207002 A1 | 7/2018 | Glerum et al. |
| 2018/0318101 A1 | 11/2018 | Engstrom |
| 2019/0029841 A1 | 1/2019 | Suh et al. |
| 2019/0053912 A1 | 2/2019 | Suddaby |

* cited by examiner

EXPANDABLE INTERVERTEBRAL FUSION IMPLANT

FIELD

The present disclosure relates to orthopedic surgery, and more particularly to an expandable and deployable intervertebral fusion implant capable of being placed within an intervertebral disc space and expanded in vertical and lateral dimensions.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae C1-C7 form the neck, support the head and neck, and allow nodding and shaking of the head. The thoracic vertebrae T1-T12 join with the ribs to form the rib cage. The five lumbar vertebrae L1-L5 carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal or neuro canal. The spinal cord and spinal nerves pass through the spinal canal, which protects them from injury. The spinal cord is the major column of nerve tissue that is connected to the brain and serves as an information super-highway between the brain and the body. The nerves in the spinal cord branch off to form pairs of nerve roots that travel through the small openings between the vertebrae and the intervertebral foramens.

Various medical conditions require a surgeon to repair, remove and/or replace the aforementioned discs. For example, in one surgical procedure, known as a discectomy (or diskectomy) with interbody fusion, the surgeon removes the nucleus of the disc and replaces it with an implant. As shown in FIG. 2, it may be necessary, for example, for the surgeon to remove the nucleus of the disc between the L3 and L4 vertebrae. Disc $D_{L3\text{-}L4}$ is shown in an enlarged view in FIG. 3. This figure also shows various anatomical structures of the spine, including facets F3A and F4A, facet joint FJ, spinous processes SP3 (not shown) and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3\text{-}L4}$. Neural canal NC is also shown. FIG. 5 is an anterior perspective view of the section of the spinal column shown in FIG. 4. FIG. 6 is a partial cross-sectional view of the section of the spinal column shown in FIG. 5, taken generally along line 6-6, but with vertebra L3 in place atop disc $D_{L3\text{-}L4}$.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, five in the lower back or lumbar region, and five in the pelvic or sacral region, which are normally fused together to form the back part of the pelvis. This column of bones is critical for providing structural support for the entire body.

Between the vertebral bones themselves exist soft tissue structures, i.e., discs, composed of fibrous tissue and cartilage that are compressible and act as shock absorbers for sudden downward forces on the upright column. The discs allow the bones to move independently of each other, as well. The repetitive forces which act on these intervertebral discs during repetitive activities of bending, lifting, and twisting cause them to break down or degenerate over time.

Presumably, because of humans' upright posture their intervertebral discs have a high propensity to degenerate. Overt trauma or covert trauma, occurring in the course of repetitive activities, disproportionately affects the more highly mobile areas of the spine. Disruption of a disc's internal architecture leads to bulging, herniation, or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal instability.

The time-honored method of addressing the issues of neural irritation and instability resulting from severe disc damage has largely focused on removal of the damaged disc and fusing the adjacent vertebral elements together. Removal of the disc relieves the mechanical and chemical irritation of neural elements, while osseous union (i.e., bone knitting) solves the problem of stability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union. Intervertebral prosthesis in various forms have therefore been used to provide immediate stability and to protect and preserve an environment that fosters growth of the grafted bone such that a structurally significant bony fusion can occur.

U.S. Pat. No. 5,505,732 (Michelson), U.S. Pat. No. 5,653,761 (Pisharodi I), U.S. Pat. No. 5,665,122 (Kambin), and U.S. Pat. No. 5,683,463 (Godefroy et al.) disclose different prior art spinal implants. The implant disclosed in U.S. Pat. No. 5,483,463 (Qin et al.) is hollow and tubular, with communicating windows in the top and bottom surfaces. External ribs, which may be serrated, stabilize the implant once it is inserted between the vertebrae. Kambin discloses an intervertebral cage that is expandable by a wedging mechanism. The degree of expansion is rather limited. Michelson and U.S. Pat. No. 5,653,762 (Pisharodi II) disclose shaft-type tools used for installing implants. The prior art devices do not enable one to achieve great ranges of implant height.

Limitations of most present-day intervertebral implants are significant and revolve largely around the marked variation in the disc space height and shape that result from either biologic variability or pathologic change. For example, if a disc space is 20 mm in height, a circular implant bridging this gap requires a minimum diameter of 20 mm just to contact the end plate of the vertebral bone. Generally, end plate disruption must occur to allow a generous bony union, meaning that an additional 2-3 mm must be added on either side resulting in a final implant size of 24-26 mm. During implantation from an anterior approach (i.e., from the front of the body), excessive retraction (or pulling) is often required on the great blood vessels, which greatly enhances the risk of devastating complications such as vascular tears or thrombosis. On the other hand, during a posterior approach, large implant diameters may require excessive traction on neural elements for adequate placement, even if all posterior bony elements are removed. In some instances, an adequate implant size cannot be inserted posteriorly, particularly if there is a significant degree of distraction required to obtain stability by tautening the annular ligamentous band. Compromising on implant size risks suboptimal stability or a loose implant, which has a greater risk of migration within, or expulsion from, the disc space. The alternative of excessively retracting neural elements to facilitate a posterior implant application results in a neuropraxia at best and permanent neural damage at worst.

U.S. Pat. No. 6,174,334 (Suddaby I) and U.S. Pat. No. 6,332,895 (Suddaby II) disclose expandable cages using a ratcheting mechanism in the perimeter to achieve expansion. The aforementioned Suddaby patents do not address issues requiring lateral expansion.

Thus, there is a long-felt need for an expandable and deployable intervertebral fusion implant capable of being placed within an intervertebral disc space and expanded in vertical and lateral dimensions.

SUMMARY

According to aspects illustrated herein, there is provided an expandable intervertebral fusion implant, comprising an inferior component, including a plate, and a first wedge slidably connected to the plate, the first wedge having a first surface, and a superior component including a second wedge, the second wedge having a second surface, wherein the first surface is operatively arranged to engage the second surface to displace the superior component relative to the inferior component.

According to aspects illustrated herein, there is provided an expandable intervertebral fusion implant, comprising an inferior component, including a first plate, a first wedge slidably connected to the first plate, the first wedge having a first surface, a second plate, a second wedge slidably connected to the second plate, the second wedge having a second surface, and at least one first cross-member connecting the first and second plates, and a superior component, including a first component including a third wedge, the third wedge having a third surface, a second component including a fourth wedge, the fourth wedge having a fourth surface, and at least one second cross-member connecting the first and second components, wherein the first and second surfaces are operatively arranged to engage the third and fourth surfaces, respectively, to displace the superior component relative to the inferior component.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

Adverting now to the figures, and as described previously, FIGS. 1-6 depict various parts and sections of spinal anatomy.

Figure 1:
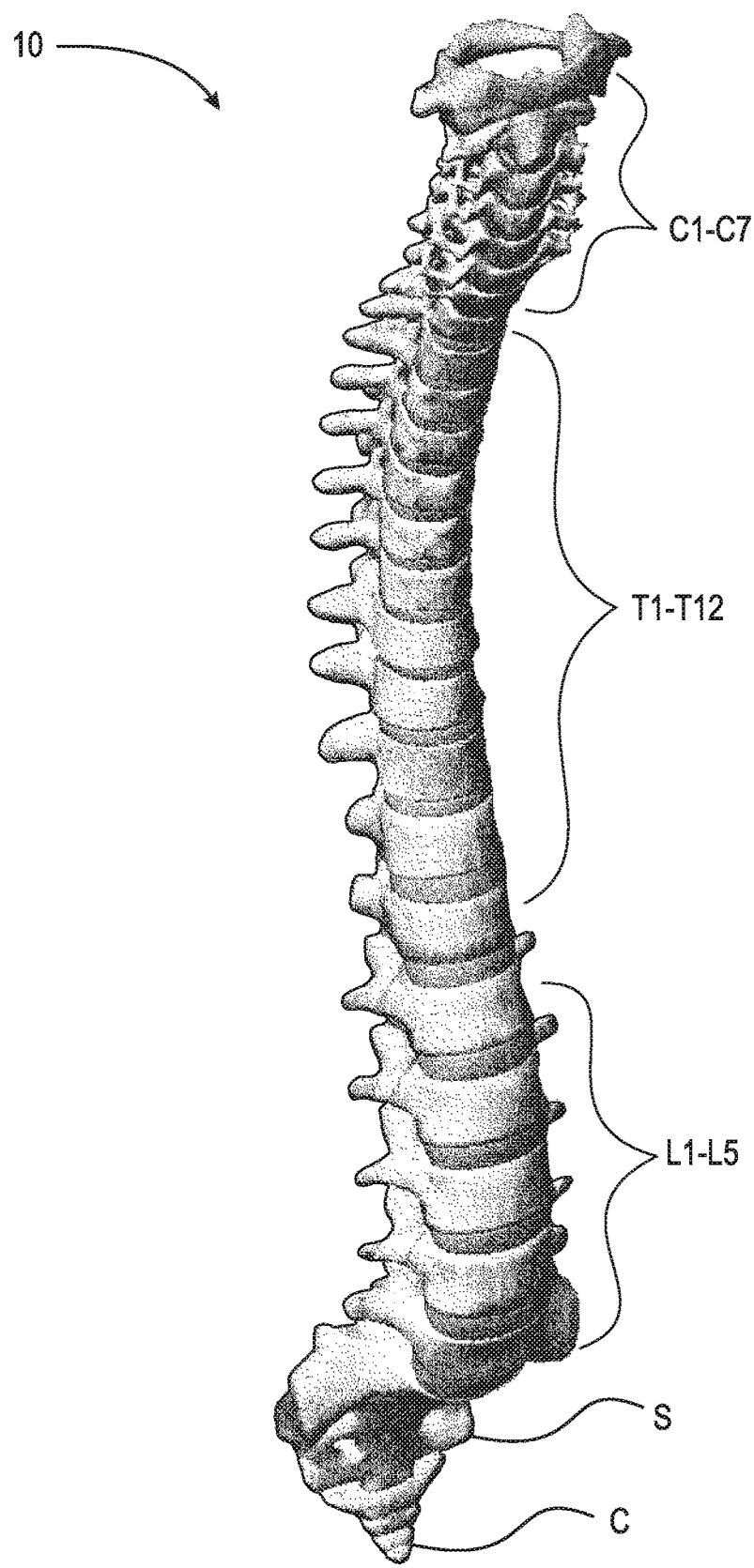
FIG. 1 is an anterior perspective view of a spinal column.
Figure 2:
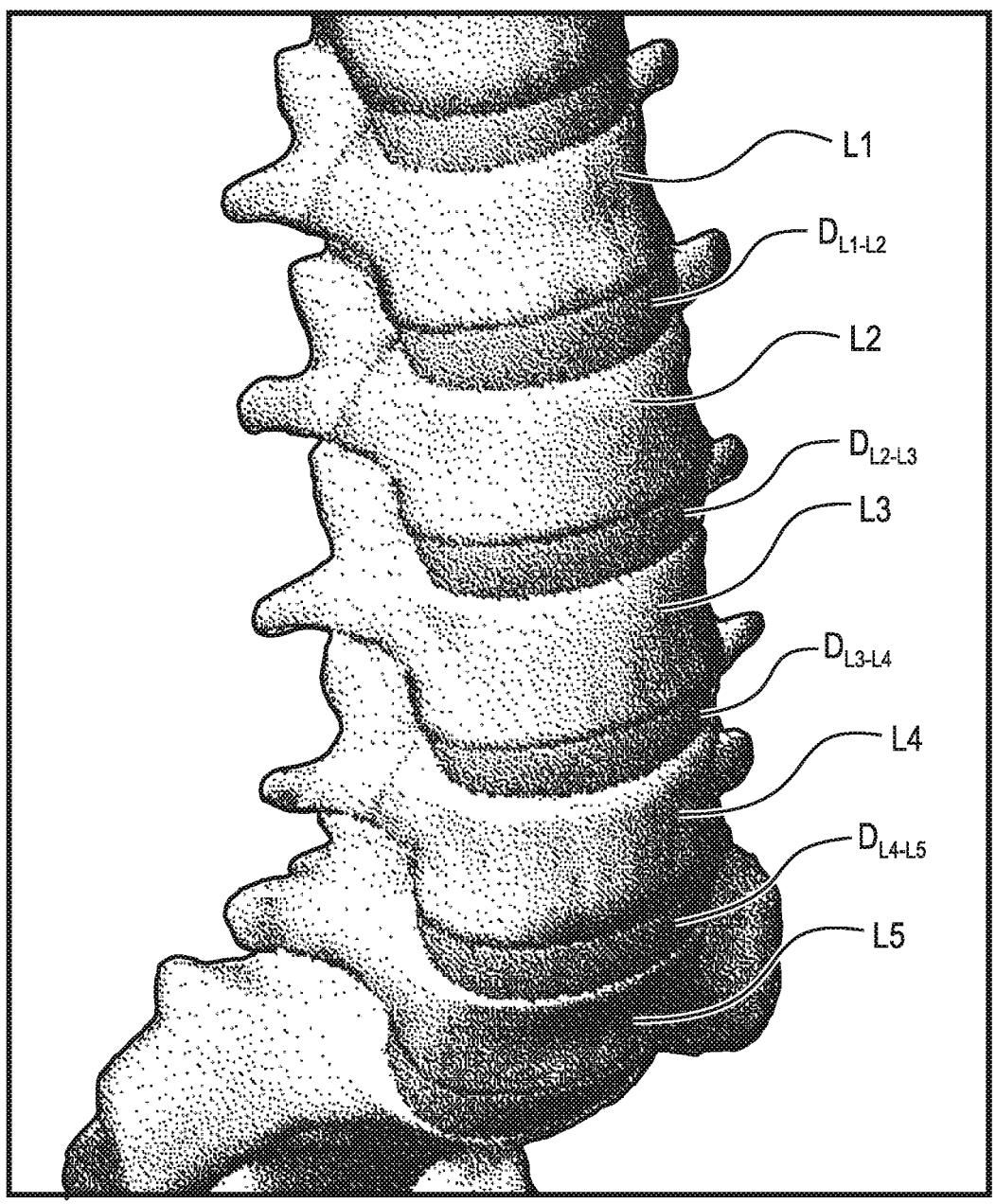
FIG. 2 is an anterior perspective view of the lumbar section of the spinal column shown in FIG. 1.
Figure 3:
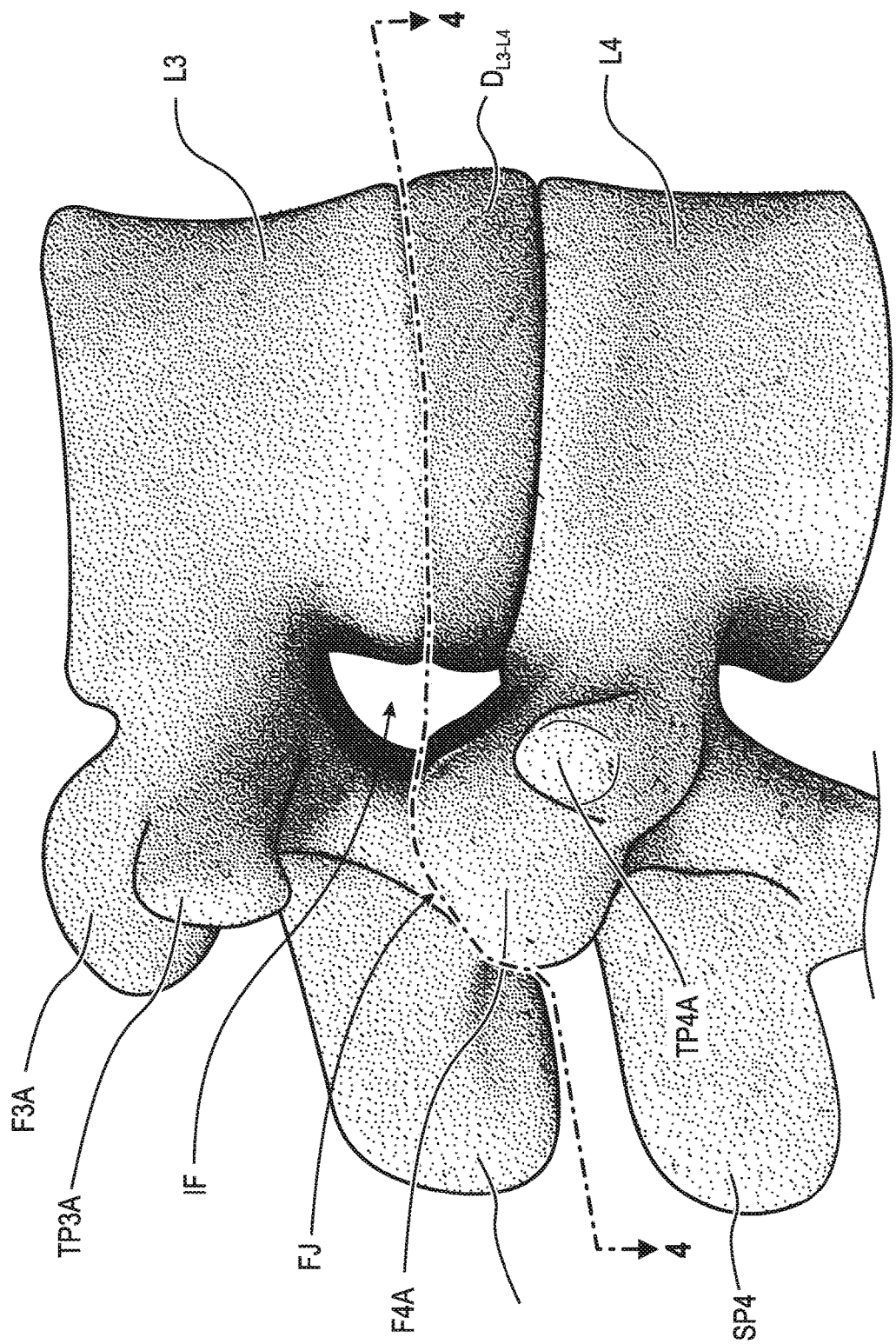
FIG. 3 is a lateral perspective view of two vertebrae, a disc, and related spinal anatomy.
Figure 4:
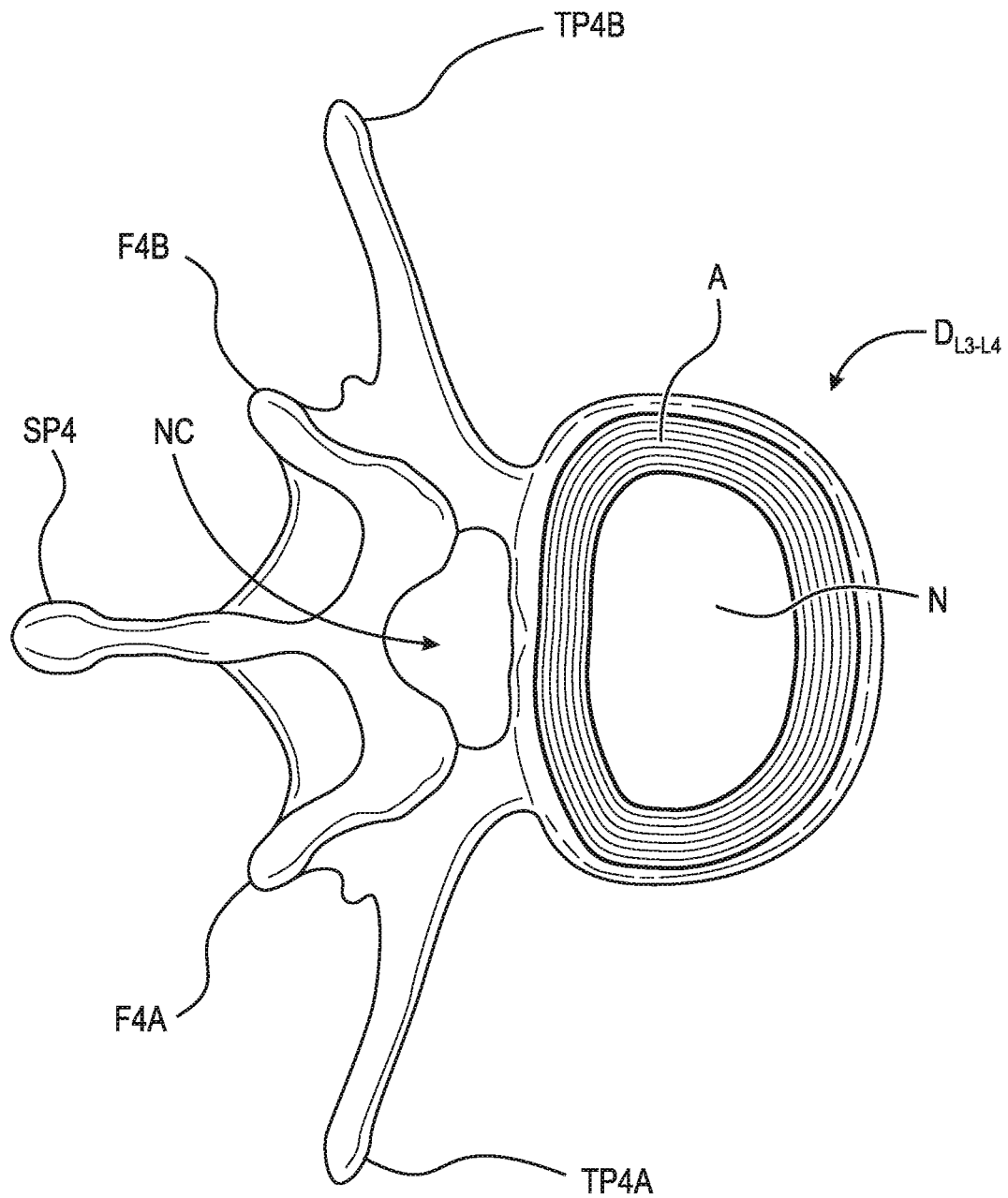
FIG. 4 is a top view of a section of the spinal column, taken generally along line 4-4 in FIG. 3.
Figure 5:
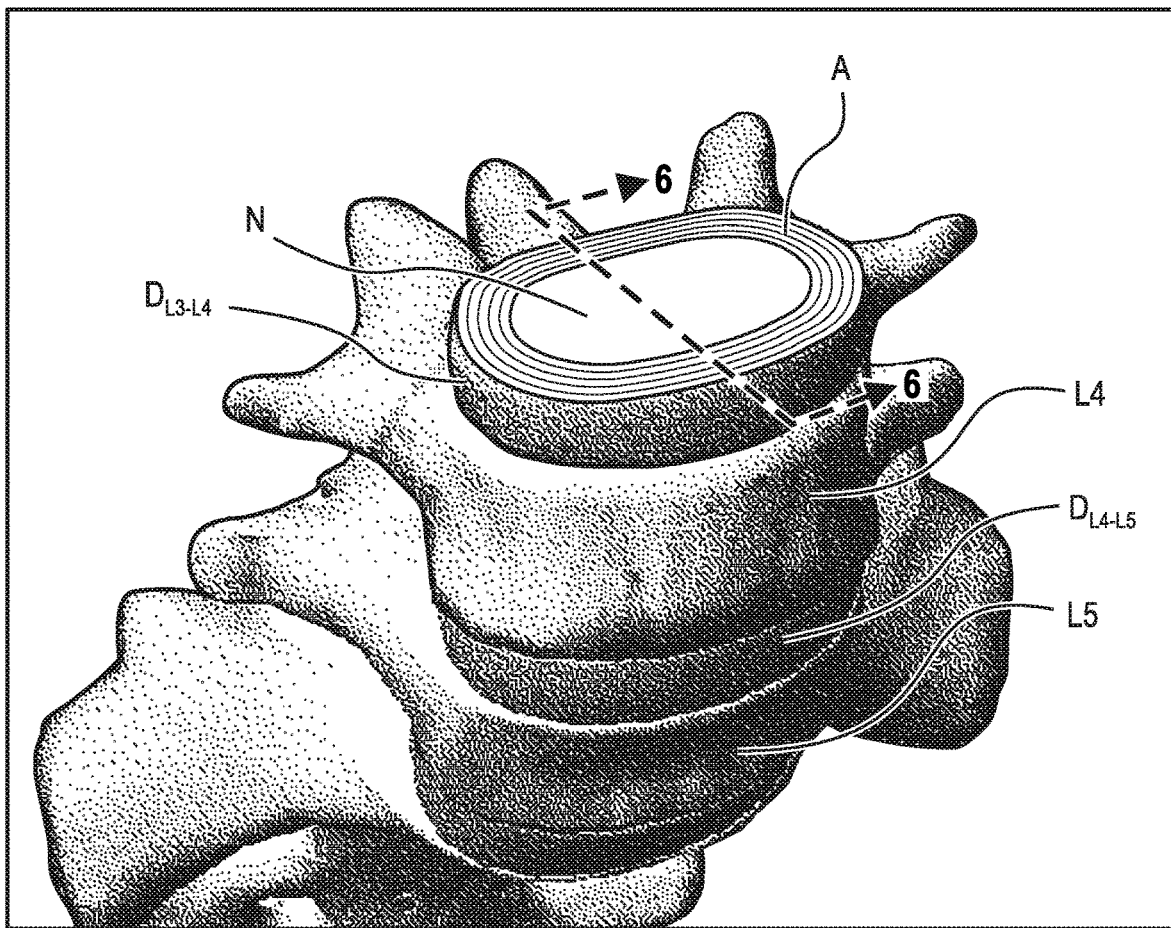
FIG. 5 is an enlarged anterior perspective view of the spinal column shown in FIG. 2, except with the top vertebra and all other structure above the top vertebra removed.
Figure 6:
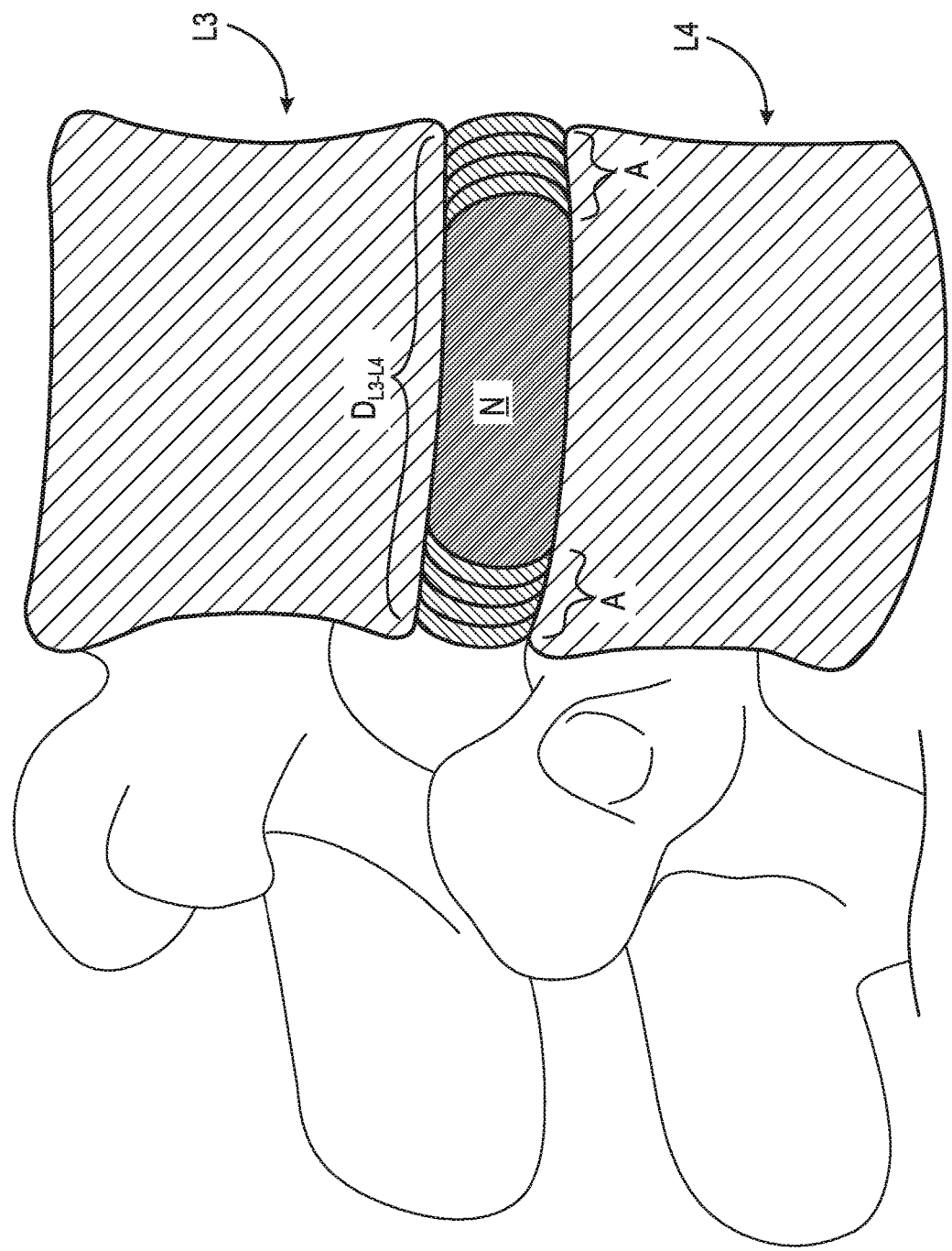
FIG. 6 is a partial cross-sectional view of the top and bottom vertebrae and disc, taken generally along line 6-6 in FIG. 5.
Figure 7:
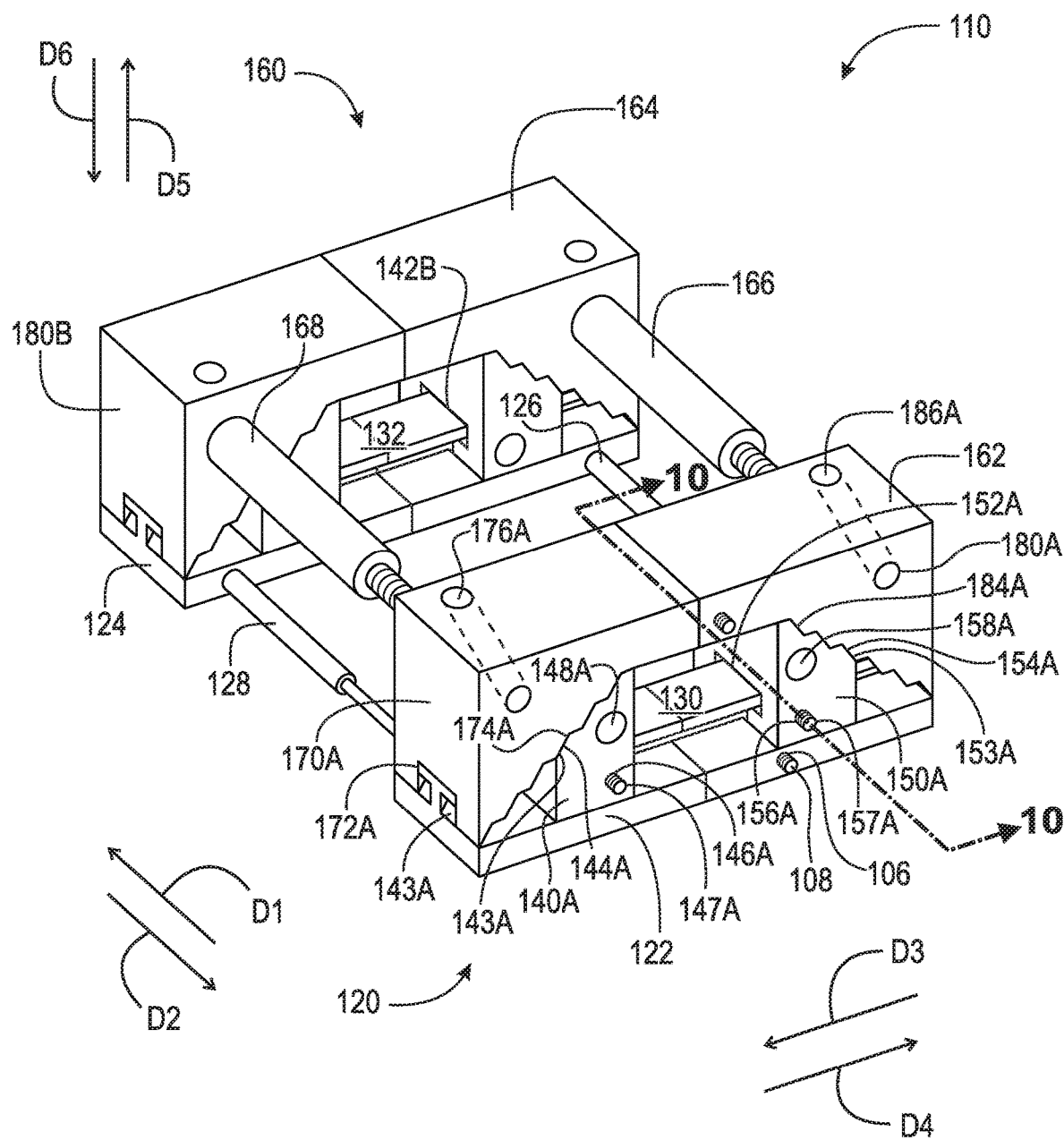
FIG. 7 is a front perspective view of an expandable intervertebral fusion implant, in a fully collapsed state.
Figure 8:
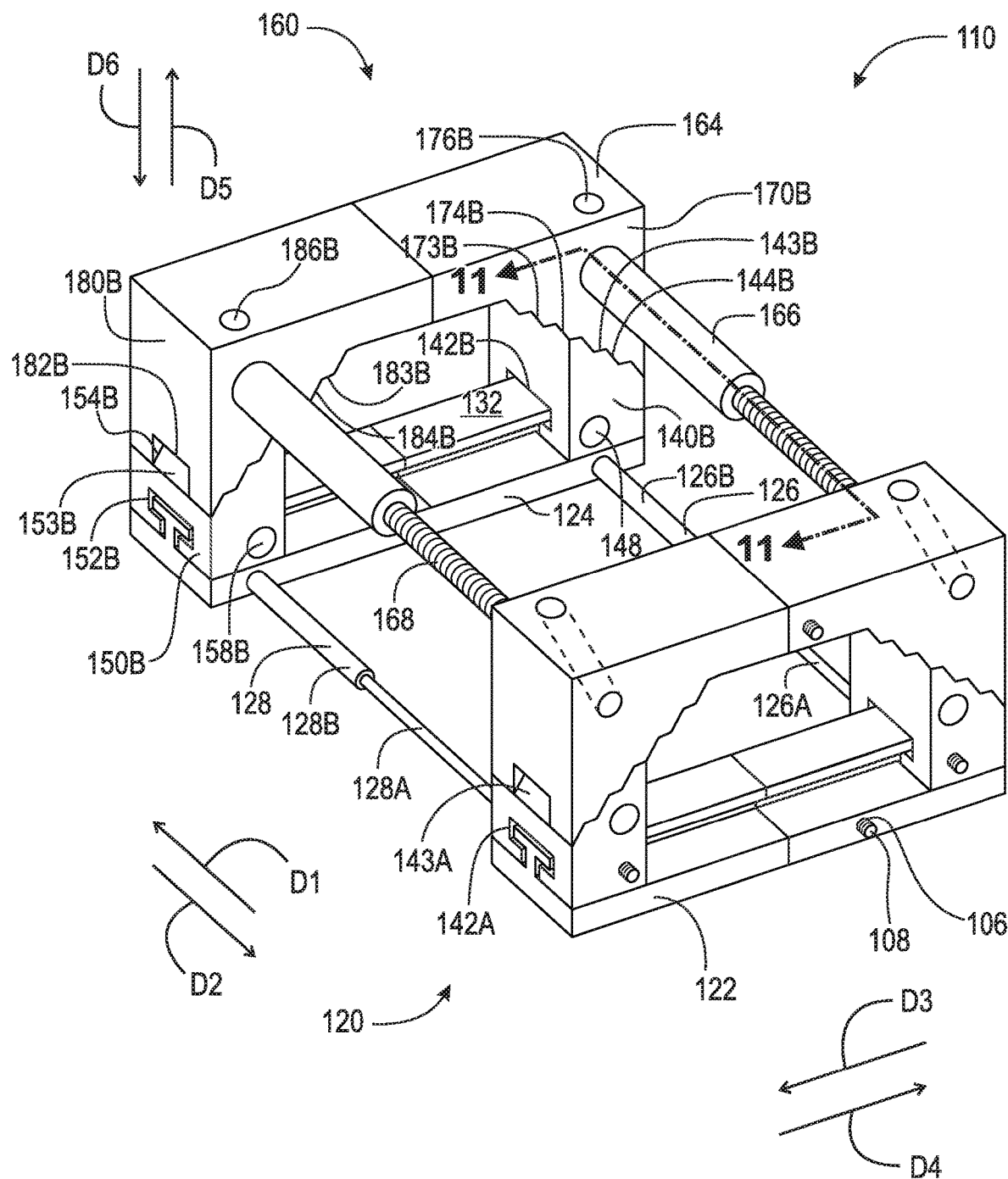
FIG. 8 is a front perspective view of the expandable intervertebral fusion implant shown in FIG. 7, in an expanded state.
Figure 9A:
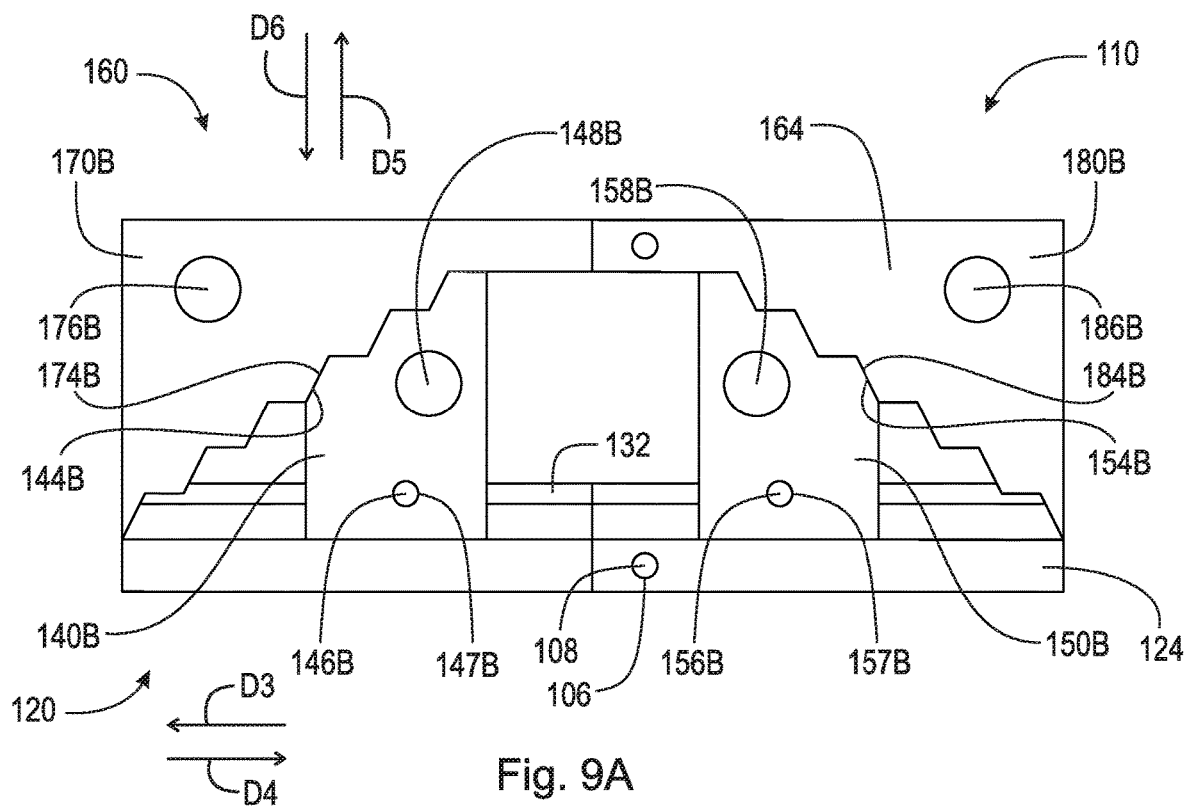
FIG. 9A is a rear elevational view of the expandable intervertebral fusion implant shown in FIG. 7.
Figure 9B:
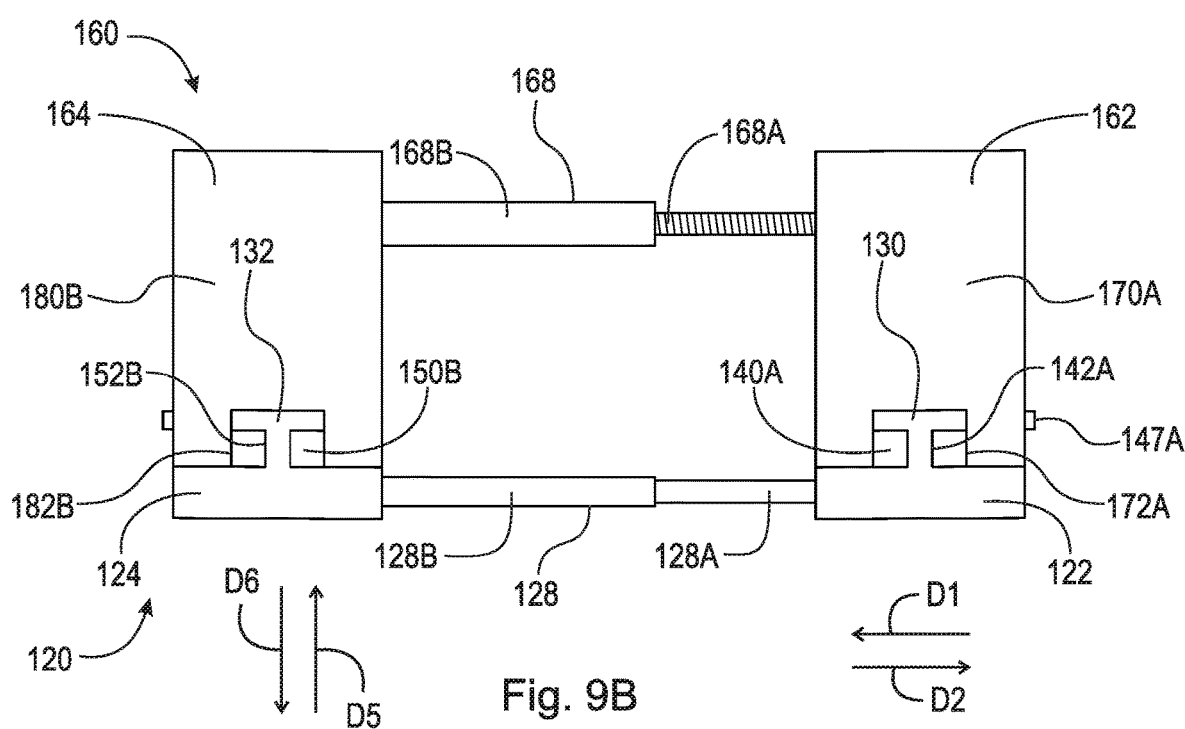
FIG. 9B is a side elevational view of the expandable intervertebral fusion implant shown in FIG. 7.

FIG. 7 is a front perspective view of expandable intervertebral fusion implant 110, in a fully collapsed state. FIG. 8 is a front perspective view of expandable intervertebral fusion implant 110, in an expanded state. FIG. 9A is a rear elevational view of expandable intervertebral fusion implant 110. FIG. 9B is a side elevational view of expandable intervertebral fusion implant 110. Expandable intervertebral fusion implant 110 generally comprises inferior component 120 and superior component 160. The following description should be read in view of FIGS. 7-9B.

Inferior component 120 comprises plate 122, plate 124, cross-member 126, cross-member 128, wedges 140A-B, and wedges 150A-B. In some embodiments, inferior component 120 comprises only plate 122, wedge 140A, and wedge 150A.

Wedges 140A and 150A are slidably engaged with plate 122. In some embodiments, and as shown in the figures, plate 122 comprises rail 130, and wedges 140A and 150A are slidably connected to rail 130. In some embodiments, plate 122 is expandable, as will be discussed in greater detail below with respect to FIG. 12.

Wedge 140A comprises groove 142A and teeth 144A arranged on angled surface 143A. In the embodiment shown in FIGS. 7-12, wedge 140A decreases in height in direction D3 (i.e., surface 143A slopes downward in direction D3). Groove 142A is operatively arranged to engage rail 130, as will be discussed in greater detail below with respect to FIG. 10. Wedge 140A is arranged to displace relative to plate 122 in direction D3 and direction D4. Teeth 144A are operatively arranged to engage teeth 174A of wedge 170A of superior component 160 to expand expandable intervertebral fusion implant 110 and lock it at a set height, as will be discussed in greater detail below. In some embodiments, teeth 144A are stairs arranged on angled surface 143A, with each step of the stairs including a tread that is parallel to directions D3 and D4 and a riser that is arranged at an angle relative to directions D3 and D4. The arrangement of teeth 144A as stairs allows expandable intervertebral fusion implant 110 to expand (i.e., by way of the engagement of the angled risers) and to at least partially lock or maintain at a certain height (i.e., by way of the engagement of the horizontal treads). The arrangement of the teeth 144A as stairs also allows expandable intervertebral fusion implant 110 to collapse. In some embodiments, teeth 144A are corrugations (i.e., ridges or grooves) arranged on angled surface 143A. Wedge 140A further comprises hole 146A and locking member 147A. As shown, locking member 147A is a set screw which engages threaded hole 146A in order to fixedly secure wedge 140A to rail 130, as will be discussed in greater detail below with respect to FIG. 10. It should be appreciated that any means suitable for fixedly securing wedge 140A to plate 122 may be used (e.g., a clamp, crimping the wedge about the rail to fixedly secure it thereto, adhesives, bolts, rivets, welding, soldering, etc.), and that the present disclosure should not be limited to just the use of a set screw. Wedge 140A may further comprise hole 148A for securing inferior component 120 to an adjacent vertebra with, for example, a bone screw. Hole 148A is arranged at an angle relative to plate 122, for example, generally in direction D6, and does not interfere with groove 142A or rail 130.

Wedge 150A comprises groove 152A and teeth 154A arranged on angled surface 153A. In the embodiment shown in FIGS. 7-12, wedge 150A decreases in height in direction D4 (i.e., surface 153A slopes downward in direction D4). Groove 152A is operatively arranged to engage rail 130, as will be discussed in greater detail below with respect to FIG. 10. Wedge 150A is arranged to displace relative to plate 122 in direction D3 and direction D4. Teeth 154A are operatively arranged to engage teeth 184A of wedge 180A of superior component 160 to expand expandable intervertebral fusion implant 110 and lock it at a set height, as will be discussed in greater detail below. In some embodiments, teeth 154A are stairs arranged on angled surface 153A, with each step of the stairs including a tread that is parallel to directions D3 and D4 and a riser that is arranged at an angle relative to directions D3 and D4. The arrangement of teeth 154A as stairs allows expandable intervertebral fusion implant 110 to expand (i.e., by way of the engagement of the angled risers) and to at least partially lock or maintain at a certain height (i.e., by way of the engagement of the horizontal treads). The arrangement of the teeth 154A as stairs also allows expandable intervertebral fusion implant 110 to collapse. In some embodiments, teeth 154A are corrugations (i.e., ridges or grooves) arranged on angled surface 153A. Wedge 150A further comprises hole 156A and locking member 157A. As shown, locking member 157A is a set screw which engages threaded hole 156A in order to fixedly secure wedge 150A to rail 130, as will be discussed in greater detail below with respect to FIG. 10. It should be appreciated that any means suitable for fixedly securing wedge 150A to plate 122 may be used (e.g., a clamp, crimping the wedge about the rail to fixedly secure it thereto, adhesives, bolts, rivets, welding, soldering, etc.), and that the present disclosure should not be limited to just the use of a set screw. Wedge 150A may further comprise hole 158A for securing inferior component 120 to an adjacent vertebra with, for example, a bone screw. Hole 158A is arranged at an angle relative to plate 122, for example, generally in direction D6, and does not interfere with groove 152A or rail 130.

Wedges 140B and 150B are slidably engaged with plate 124. In some embodiments, and as shown in the figures, plate 124 comprises rail 132, and wedges 140B and 150B are slidably connected to rail 132. In some embodiments, plate 124 is expandable, as will be discussed in greater detail below with respect to FIG. 12.

Wedge 140B comprises groove 142B and teeth 144B arranged on angled surface 143B. In the embodiment shown in FIGS. 7-12, wedge 140B decreases in height in direction D4 (i.e., surface 143B slopes downward in direction D3). Groove 142B is operatively arranged to engage rail 132, as will be discussed in greater detail below with respect to FIG. 10. Wedge 140B is arranged to displace relative to plate 124 in direction D3 and direction D4. Teeth 144B are operatively arranged to engage teeth 174B of wedge 170B of superior component 160 to expand expandable intervertebral fusion implant 110 and lock it at a set height, as will be discussed in greater detail below. In some embodiments, teeth 144B are stairs arranged on angled surface 143B, with each step of the stairs including a tread that is parallel to directions D3 and D4 and a riser that is arranged at an angle relative to directions D3 and D4. The arrangement of teeth 144B as stairs allows expandable intervertebral fusion implant 110 to expand (i.e., by way of the engagement of the angled risers) and to at least partially lock or maintain at a certain height (i.e., by way of the engagement of the horizontal treads). The arrangement of the teeth 144B as stairs also allows expandable intervertebral fusion implant 110 to collapse. In some embodiments, teeth 144B are corrugations (i.e., ridges or grooves) arranged on angled surface 143B. Wedge 140B further comprises hole 146B and locking member 147B (see FIG. 9A). As shown, locking member 147B is a set screw which engages threaded hole 146B in order to fixedly secure wedge 140B to rail 132, as will be discussed in greater detail below with respect to FIG. 10. It should be appreciated that any means suitable for fixedly securing wedge 140B to plate 124 may be used (e.g., a clamp, crimping the wedge about the rail to fixedly secure it thereto, adhesives, bolts, rivets, welding, soldering, etc.), and that the present disclosure should not be limited to just the use of a set screw. Wedge 140B may further comprise hole 148B for securing inferior component 120 to an adjacent vertebra with, for example, a bone screw. Hole 148B is arranged at an angle relative to plate 124, for example, generally in direction D6, and does not interfere with groove 142B or rail 132.

Wedge 150B comprises groove 152B and teeth 154B arranged on angled surface 153B. In the embodiment shown in FIGS. 7-12, wedge 150B decreases in height in direction D3 (i.e., surface 153A slopes downward in direction D4). Groove 152B is operatively arranged to engage rail 132, as will be discussed in greater detail below with respect to FIG. 10. Wedge 150B is arranged to displace relative to plate 124 in direction D3 and direction D4. Teeth 154B are operatively arranged to engage teeth 184B of wedge 180B of superior component 160 to expand expandable intervertebral fusion implant 110 and lock it at a set height, as will be discussed in greater detail below. In some embodiments, teeth 154B are stairs arranged on angled surface 153B, with each step of the stairs including a tread that is parallel to directions D3 and D4 and a riser that is arranged at an angle relative to directions D3 and D4. The arrangement of teeth 154B as stairs allows expandable intervertebral fusion implant 110 to expand (i.e., by way of the engagement of the angled risers) and to at least partially lock or maintain at a certain height (i.e., by way of the engagement of the horizontal treads). The arrangement of the teeth 154B as stairs also allows expandable intervertebral fusion implant 110 to collapse. In some embodiments, teeth 154B are corrugations (i.e., ridges or grooves) arranged on angled surface 153B. Wedge 150B further comprises hole 156B and locking member 157B (see FIG. 9A). As shown, locking member 157B is a set screw which engages threaded hole 156B in order to fixedly secure wedge 150B to rail 132, as will be discussed in greater detail below with respect to FIG. 10. It should be appreciated that any means suitable for fixedly securing wedge 150B to plate 124 may be used (e.g., a clamp, crimping the wedge about the rail to fixedly secure it thereto, adhesives, bolts, rivets, welding, soldering, etc.), and that the present disclosure should not be limited to just the use of a set screw. Wedge 150B may further comprise hole 158B for securing inferior component 120 to an adjacent vertebra with, for example, a bone screw. Hole 158B is arranged at an angle relative to plate 124, for example, generally in direction D6, and does not interfere with groove 152B or rail 132.

Cross-members 126 and 128 connect plate 124 to plate 122. In some embodiments, cross-members 126 and 128 are telescoping cross-members and allow for expandable intervertebral fusion implant 110 to be expanded and collapsed. For example, cross-members may comprise an inner rod displaceable (or slidable) within an outer rod. Plate 124 may be displaced relative to plate 122 in direction D1 to expand expandable intervertebral fusion implant 110, specifically inferior component 120, and direction D2 to collapse expandable intervertebral fusion implant 110, specifically inferior component 120. Cross-members 126 and 128 are fixed to respective ends, or proximate ends, of plates 122 and 124. It should be appreciated that cross-members 126 and 128 do not have to be fixed at the ends of plates 122 and 124, but rather can be fixed axially inward from the ends of plates 122 and 124. In some embodiments, inferior component 120 comprises one cross-member that connects plates 122 and 124. In some embodiments, inferior component 120 does not comprise any cross-members. In some embodiments, inferior component 120 comprises one or more cross-members connecting plates 122 and 124, for example, three cross-members. It should be appreciated that although the drawings depict cross-members 126 and 128 having a circular cross-sectional geometry, any geometry suitable for expandably or displaceably connecting plates 122 and 124 may be used, for example, square, rectangular, triangular, ellipsoidal, etc. In some embodiments, cross-members 126 and 128 may be threaded (or locking) telescoping cross-members, similar or equivalent to cross-members 166 and 168 discussed in greater detail below. Additionally, it should be appreciated that in some embodiments, cross-members 126 and 128 are not telescoping and connect plate 124 to plate 122 at a set distance.

Superior component 160 comprises component 162, component 164, cross-member 166, cross-member 168, wedges 170A-B, and wedges 180A-B. In some embodiments, superior component 160 comprises only component 162, wedge 170A, and wedge 180A.

Wedges 170A and 180A are connected to component 122. Wedge 170A comprises channel 172A and teeth 174A arranged on angled surface 173A. In the embodiment shown in FIGS. 9-12, wedge 170A decreases in height in direction D4 (i.e., surface 173A slopes downward in direction D4). Channel 172A is operatively arranged to engage rail 130 in a fully collapsed position, as is shown in FIG. 7. Channel 172A allows superior component 160 to fully collapse with respect to inferior component 120 (i.e., such that wedges 170A and 180A and wedges 170B and 180B rest on plates 122 and 124, respectively). Angled surface 173A is operatively arranged to engage angled surface 143A to expand superior component 160 with respect to inferior component 120. Specifically, as wedge 140A is displaced in direction D3 relative to plate 122, angled surface 143A engages angled surface 173A to displace superior component 160 in direction D5 relative to inferior component 120. Teeth 174A are operatively arranged to engage teeth 144A to lock superior component 160 at a distance relative to inferior component 120. Specifically, teeth 174A engage teeth 144A to allow wedge 140A to displace in direction D3 relative to plate 122, and at the same time, if required, allow wedge 140A to displace in direction D4 relative to plate 122. Such arrangement allows expandable intervertebral fusion implant 110 to expand and collapse in a controlled fashion. In some embodiments, teeth 174A are stairs arranged on angled surface 173A, with each step of the stairs including a tread that is parallel to directions D3 and D4 and a riser that is arranged at an angle relative to directions D3 and D4. The arrangement of teeth 174A as stairs allows expandable intervertebral fusion implant 110 to expand (i.e., by way of the engagement of the angled risers) and to at least partially lock or maintain at a certain height (i.e., by way of the engagement of the horizontal treads). The arrangement of the teeth 174A as stairs also allows expandable intervertebral fusion implant 110 to collapse. In some embodiments, teeth 174A are corrugations (i.e., ridges or grooves) arranged on angled surface 173A. Wedge 170A may further comprise hole 176A for securing superior component 160 to an adjacent vertebra with, for example, a bone screw. Hole 176A is arranged at an angle relative to plate 122, for example, generally in direction D5.

Wedge 180A comprises channel 182A and teeth 184A arranged on angled surface 183A. In the embodiment shown in FIGS. 9-12, wedge 180A decreases in height in direction D3 (i.e., surface 183A slopes downward in direction D3). Channel 182A is operatively arranged to engage rail 130 in a fully collapsed position, as is shown in FIG. 7. Channel 182A allows superior component 160 to fully collapse with respect to inferior component 120 (i.e., such that wedges 170A and 180A and wedges 170B and 180B rest on plates 122 and 124, respectively). Angled surface 183A is operatively arranged to engage angled surface 153A to expand superior component 160 with respect to inferior component 120. Specifically, as wedge 150A is displaced in direction D4 relative to plate 122, angled surface 153A engages angled surface 183A to displace superior component 160 in direction D5 relative to inferior component 120. Teeth 184A are operatively arranged to engage teeth 154A to lock superior component 160 at a distance relative to inferior component 120. Specifically, teeth 184A engage teeth 154A to allow wedge 150A to displace in direction D4 relative to plate 122, and at the same time, if required, allow wedge 150A to displace in direction D3 relative to plate 122. Such arrangement allows expandable intervertebral fusion implant 110 to expand and collapse in a controlled fashion. In some embodiments, teeth 184A are stairs arranged on angled surface 183A, with each step of the stairs including a tread that is parallel to directions D3 and D4 and a riser that is arranged at an angle relative to directions D3 and D4. The arrangement of teeth 184A as stairs allows expandable intervertebral fusion implant 110 to expand (i.e., by way of the engagement of the angled risers) and to at least partially lock or maintain at a certain height (i.e., by way of the engagement of the horizontal treads). The arrangement of the teeth 184A as stairs also allows expandable intervertebral fusion implant 110 to collapse. In some embodiments, teeth 184A are corrugations (i.e., ridges or grooves) arranged on angled surface 183A. Wedge 180A may further comprise hole 186A for securing superior component 160 to an adjacent vertebra with, for example, a bone screw. Hole 186A is arranged at an angle relative to plate 122, for example, generally in direction D5.

Wedge 170B comprises channel 172B and teeth 174B arranged on angled surface 173B. In the embodiment shown in FIGS. 7-12, wedge 170B decreases in height in direction D3 (i.e., surface 173B slopes downward in direction D3). Channel 172B is operatively arranged to engage rail 132 in a fully collapsed position, as is shown in FIG. 7. Channel 172B allows superior component 160 to fully collapse with respect to inferior component 120 (i.e., such that wedges 170A and 180A and wedges 170B and 180B rest on plates 122 and 124, respectively). Angled surface 173B is operatively arranged to engage angled surface 143B to expand superior component 160 with respect to inferior component 120. Specifically, as wedge 140B is displaced in direction D4 relative to plate 124, angled surface 143B engages angled surface 173B to displace superior component 160 in direction D5 relative to inferior component 120. Teeth 174B are operatively arranged to engage teeth 144B to lock superior component 160 at a distance relative to inferior component 120. Specifically, teeth 174B engage teeth 144B to allow wedge 140B to displace in direction D4 relative to plate 122, and at the same time, if required, allow wedge 140B to displace in direction D3 relative to plate 124. Such arrangement allows expandable intervertebral fusion implant 110 to expand and collapse in a controlled fashion. In some embodiments, teeth 174B are stairs arranged on angled surface 173B, with each step of the stairs including a tread that is parallel to directions D3 and D4 and a riser that is arranged at an angle relative to directions D3 and D4. The arrangement of teeth 174B as stairs allows expandable intervertebral fusion implant 110 to expand (i.e., by way of the engagement of the angled risers) and to at least partially lock or maintain at a certain height (i.e., by way of the engagement of the horizontal treads). The arrangement of the teeth 174B as stairs also allows expandable intervertebral fusion implant 110 to collapse. In some embodiments, teeth 174B are corrugations (i.e., ridges or grooves) arranged on angled surface 173B. Wedge 170B may further comprise hole 176B for securing superior component 160 to an adjacent vertebra with, for example, a bone screw. Hole 176B is arranged at an angle relative to plate 124, for example, generally in direction D5.

Wedge 180B comprises channel 182B and teeth 184B arranged on angled surface 183B. In the embodiment shown in FIGS. 7-12, wedge 180B decreases in height in direction D4 (i.e., surface 183B slopes downward in direction D4). Channel 182B is operatively arranged to engage rail 132 in a fully collapsed position, as is shown in FIG. 7. Channel 182B allows superior component 160 to fully collapse with respect to inferior component 120 (i.e., such that wedges 170A and 180A and wedges 170B and 180B rest on plates 122 and 124, respectively). Angled surface 183B is operatively arranged to engage angled surface 153B to expand superior component 160 with respect to inferior component 120. Specifically, as wedge 150B is displaced in direction D3 relative to plate 124, angled surface 153B engages angled surface 183B to displace superior component 160 in direction D5 relative to inferior component 120. Teeth 184B are operatively arranged to engage teeth 154B to lock superior component 160 at a distance relative to inferior component 120. Specifically, teeth 184B engage teeth 154B to allow wedge 150B to displace in direction D3 relative to plate 124, and at the same time, if required, allow wedge 150B from displacing in direction D4 relative to plate 124. Such arrangement allows expandable intervertebral fusion implant 110 to expand and collapse in a controlled fashion. In some embodiments, teeth 184B are stairs arranged on angled surface 183B, with each step of the stairs including a tread that is parallel to directions D3 and D4 and a riser that is arranged at an angle relative to directions D3 and D4. The arrangement of teeth 184B as stairs allows expandable intervertebral fusion implant 110 to expand (i.e., by way of the engagement of the angled risers) and to at least partially lock or maintain at a certain height (i.e., by way of the engagement of the horizontal treads). The arrangement of the teeth 184B as stairs also allows expandable intervertebral fusion implant 110 to collapse. In some embodiments, teeth 184B are corrugations (i.e., ridges or grooves) arranged on angled surface 183B. Wedge 180B may further comprise hole 186B for securing superior component 160 to an adjacent vertebra with, for example, a bone screw. Hole 186B is arranged at an angle relative to plate 124, for example, generally in direction D5.

Cross-members 166 and 168 connect component 164 to component 162. In some embodiments, cross-members 166 and 168 are telescoping cross-members and allow for expandable intervertebral fusion implant 110 to be expanded and collapsed. For example, cross-members may comprise an inner rod displaceable (or slidable) within an outer rod. Component 164 may be displaced relative to component 162 in direction D1 to expand expandable intervertebral fusion implant 110, specifically superior component 160, and direction D2 to collapse expandable intervertebral fusion implant 110, specifically superior component 160. Cross-members 166 and 168 are fixed to respective ends, or proximate ends, of components 162 and 164. It should be appreciated that cross-members 166 and 168 do not have to be fixed at the ends of components 162 and 164, but rather can be fixed axially inward from the ends of components 162 and 164. In some embodiments, superior component 160 comprises one cross-member that connects components 162 and 164. In some embodiments, superior component 160 does not comprise any cross-members. In some embodiments, superior component 160 comprises one or more cross-members connecting components 162 and 164, for example, three cross-members. In some embodiments, cross-members 166 and 168 are threadably engaged, as will be discussed in greater detail below with respect to FIG. 11. It should be appreciated that although the drawings depict cross-members 166 and 168 having a circular cross-sectional geometry, any geometry suitable for expandably or displaceably connecting components 162 and 164 may be used, for example, square, rectangular, triangular, ellipsoidal, etc. Additionally, it should be appreciated that in some embodiments, cross-members 166 and 168 are not telescoping and connect component 164 to component 162 at a set distance.

FIG. 9B is a side elevational view of expandable intervertebral fusion implant 110 in a fully collapsed state as shown in FIG. 7. Cross-members 168 and 128, along with cross-members 126 and 166 (not shown in FIG. 9B) are telescoping such that expandable intervertebral fusion implant 110 is expandable in the anterior-posterior directions (i.e., directions D1 and D2). Cross-member 168 comprises inner rod 168A arranged to threadably engage outer rod 168B. Cross-member 168 may comprise threading operatively arranged to expand and contract expandable intervertebral fusion implant 110, and lock inner rod 168A and outer rod 168B at a set length. The threadable engagement of inner rod 168A and outer rod 168B will be discussed in greater detail below. Cross-member 128 comprises inner rod 128A arranged to slidingly engage outer rod 128B. Cross-member 128 may further comprise threading or a plurality of pins arranged to lock inner rod 128A and outer rod 128B at a set length. Cross-members 126 and 166 are arranged substantially similar to cross-members 128 and 168. For example, cross-member 126 comprises inner rod 126A arranged to slidingly engage outer rod 126B, and may further comprise threading or a plurality of pins arranged to lock inner rod 126A and outer rod 126B at a set length. Cross-member 166 comprises inner rod 166A arranged to slidingly engage outer rod 166B, and may further comprise threading or a plurality of pins arranged to lock inner rod 166A and outer rod 166B at a set length (as is discussed in greater detail with respect to FIG. 11 below).

Also shown in FIG. 9B are rails 130 and 132 arranged on plates 122 and 124, respectively. Grooves 142A and 152B of wedges 140A and 150B engage rails 130 and 132, respectively, and grooves 152A and 142B of wedges 150A and 140B engage rails 130 and 132, respectively (not shown in FIG. 10B). Furthermore, in the fully collapsed position, channels 172A and 182B of wedges 170A and 180B engage rails 130 and 132, respectively, and channels 182A and 172B of wedges 180A and 170B engage rails 130 and 132, respectively (not shown).

Figure 10:
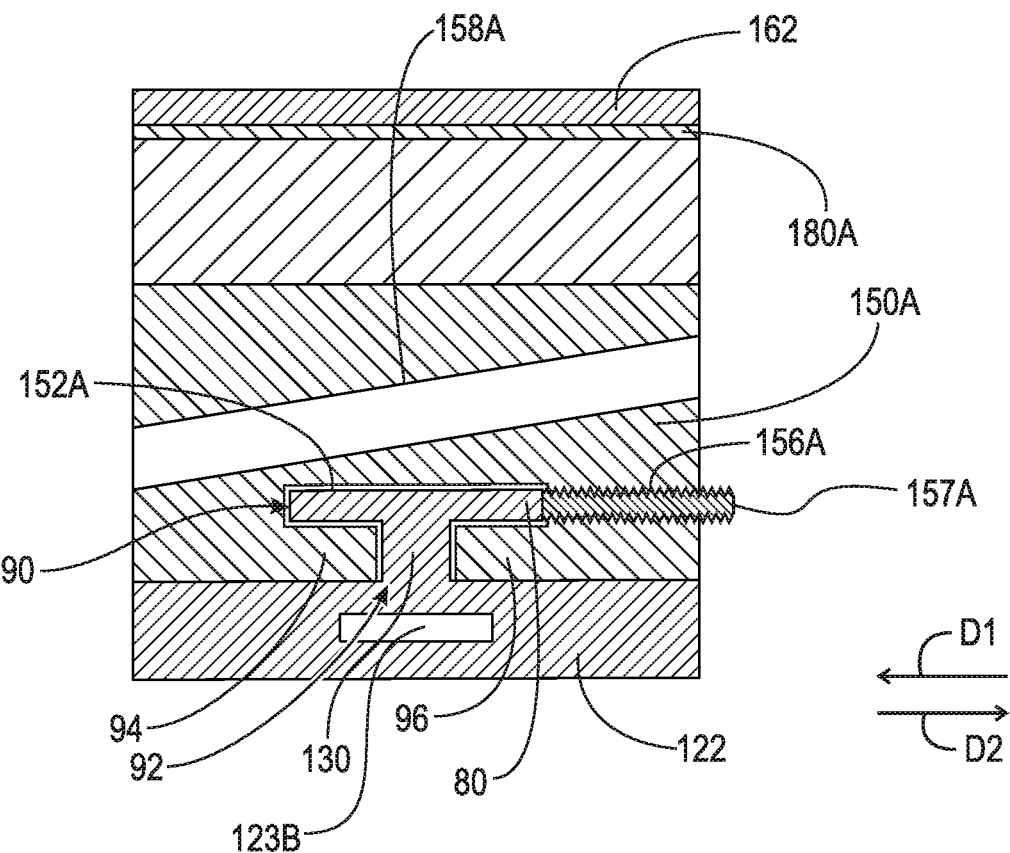
FIG. 10 is a cross-sectional view of a tongue and groove connection taken generally along line 10-10 in FIG. 7.

FIG. 10 is a cross-sectional view of a tongue and groove connection taken generally along line 10-10 in FIG. 7. Groove 152A of wedge 150A generally comprises channel 90, opening 92, and sides 94 and 96. Rail 130 of plate 122 comprises runner 80. Groove 152A is arranged to enclose runner 80, such that wedge 150A and plate 122 are slidably connected. It should be appreciated that wedge 140A and wedges 140B and 150B are arranged substantially similar to wedge 150A with respect to engagement with respective rails 130 and 132. Specifically, groove 142A of wedge 140A slidably engages runner 80 of rail 130. Similarly, grooves 142B and 152B of wedges 140B and 150B slidably engage the runner of rail 132.

Also shown in FIG. 10 is locking member or screw 157A arranged in hole 156A and engaged with rail 130. FIG. 10 shows wedge 150A in a locked position relative to rail 130. Specifically, screw 157A has been tightened within hole 156A (i.e., screw 157A is displaced in direction D1) such that screw 157A abuts against runner 80. The frictional force between screw 157A and runner 80 prevents displacement of wedge 150A with respect to plate 122. When screw 157A is loosened within hole 156A (i.e., screw 157A is displaced in direction D2) such that screw 157A no longer abuts against runner 80, wedge 150A is again displaceable relative to plate 122. It should be appreciated that locking member or screw 147A and locking members or screws 147B and 157B are arranged to engage rails 130 and 132, respectively, in a substantially similar fashion to that of locking member or screw 157 as described above. In some embodiments, plate 122 is expandable and comprises an extension which engages hole 123B, which will be discussed in greater detail with respect to FIG. 12.

Figure 11:
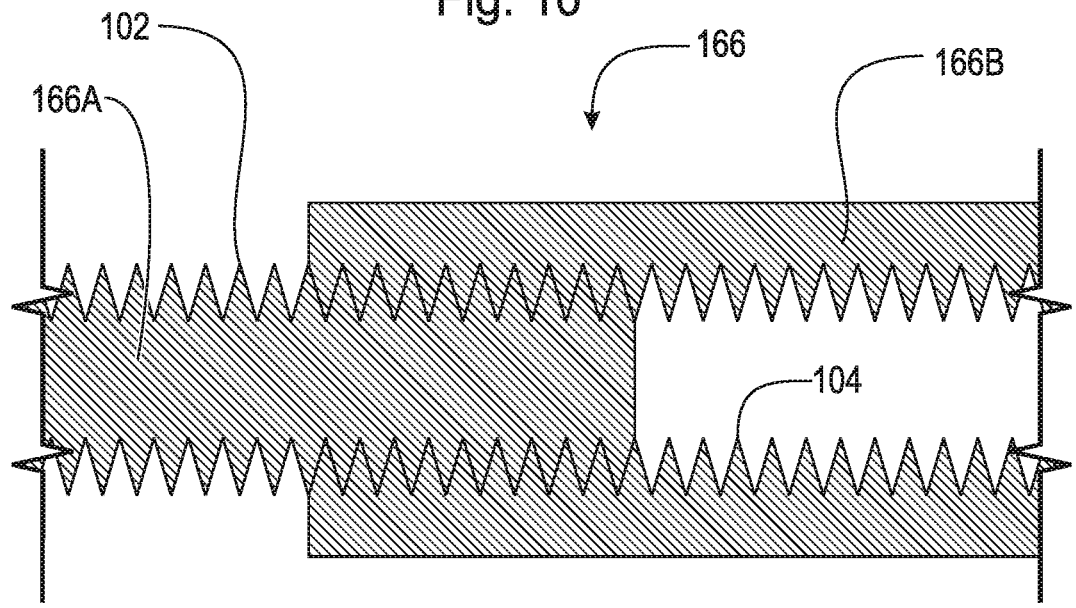
FIG. 11 is a cross-sectional view of a cross-member taken generally along line 11-11 in FIG. 8.

FIG. 11 is a cross-sectional view of cross-member 166 taken generally along line 11-11 in FIG. 8. As previously discussed, cross-member 166 comprises inner rod 166A arranged to displaceably (e.g., threadably) engage outer rod 166B. In the embodiment shown, inner rod 166A comprises outer threading 102 and outer rod 166B comprises inner threading 104. Outer threading 102 engages inner threading 104 to expand and contract expandable intervertebral fusion implant 110. For example, as inner rod 166A is rotated in a first circumferential direction, outer rod 166B displaces relative to inner rod 166A in direction D1, thereby expanding expandable intervertebral fusion implant 110. As inner rod 166A is rotated in a second circumferential direction, outer rod 166B displaces relative to inner rod 166A in direction D2, thereby contracting or collapsing expandable intervertebral fusion implant 110. Similarly, as outer rod 166B is rotated in a first circumferential direction, inner rod 166A displaces relative to outer rod 166B in direction D2, thereby expanding expandable intervertebral fusion implant 110. As outer rod 166B is rotated in a second circumferential direction, inner rod 166A displaces relative to outer rod 166B in direction D1, thereby contracting or collapsing expandable intervertebral fusion implant 110. As such, in some embodiments, one of inner rod 166A and outer rod 166B is fixedly secured to superior component 160, and the other is rotatably secured to superior component 160 (i.e., inner rod 166A must be able to be rotated relative to the outer rod 166B or vice versa). In some embodiments, at least one of inner rod 166A and outer rod 166B is rotatably secured to superior component 160 or inferior component 120. This similar locking mechanism (i.e., threading) may be used on cross-members 126, 128, and 168. It should be appreciated that telescoping members are known in the art and that any suitable telescoping design may be used. In an example embodiment, one or more cross-members have a locking mechanism. In an example embodiment, no cross-members have a locking mechanism.

Figure 12:
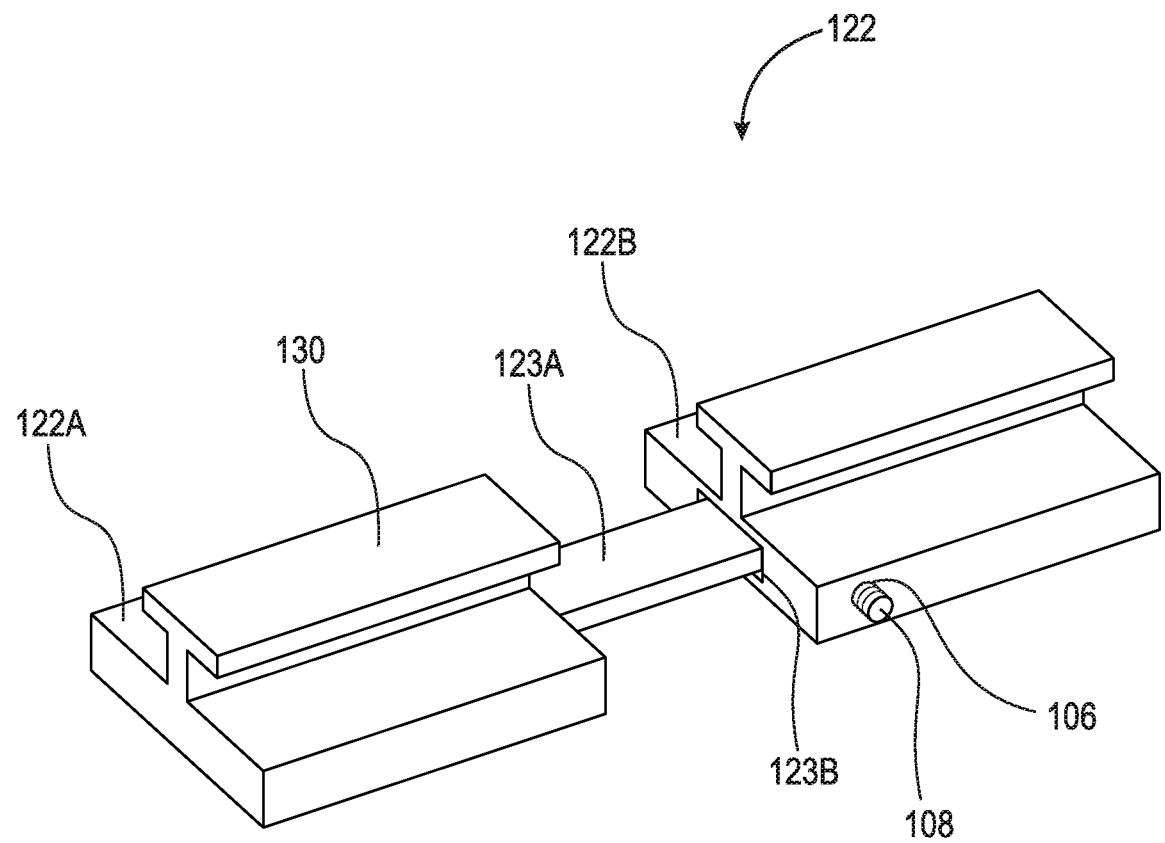
FIG. 12 is a perspective view of a plate in an expanded state.
Figure 12:
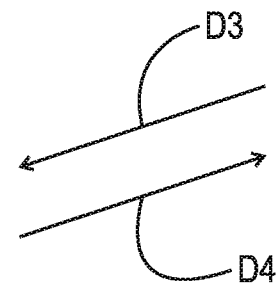

FIG. 12 is a perspective view of plate 122, in an expanded state. It should be appreciated that plate 124, and plates 222 and 224 (discussed below), may comprise a substantially similar or the same design as plate 122 as described in FIG. 12. In the embodiment shown, plate 122 comprises section 122A, section 122B, and rail 130. Section 122B is operatively arranged to displace relative to section 122B in direction D4 to expand plate 122, and in direction D3 to collapse plate 122. In some embodiments, section 122A comprises extension 123A which slidably engages hole 123B of section 122B. One of sections 122A and 122B may further comprise a locking mechanism. In the embodiment shown, section 122B comprises hole 106 and screw 108 (e.g., a set screw), which is operatively arranged to engage extension 123A to lock section 122B at a set distance from section 122A. It should be appreciated that plate 122 may use any known expansion mechanism or means for expansion. It should further be appreciated that plate 122 may use any known locking mechanism to lock section 122B at a set distance from section 122A.

In some embodiments, components 162, 164, 262, and 264 comprise a similar design to plate 122, namely, that each of components 162, 164, 262, and 264 are laterally expandable. For example, each of components 162, 164, 262, and 264 may comprise a first section including an extension and a second section including a hole, the extension is operatively arranged to slidably engage the hole, and the two sections are locked via a set screw (see FIG. 12).

Figure 13:
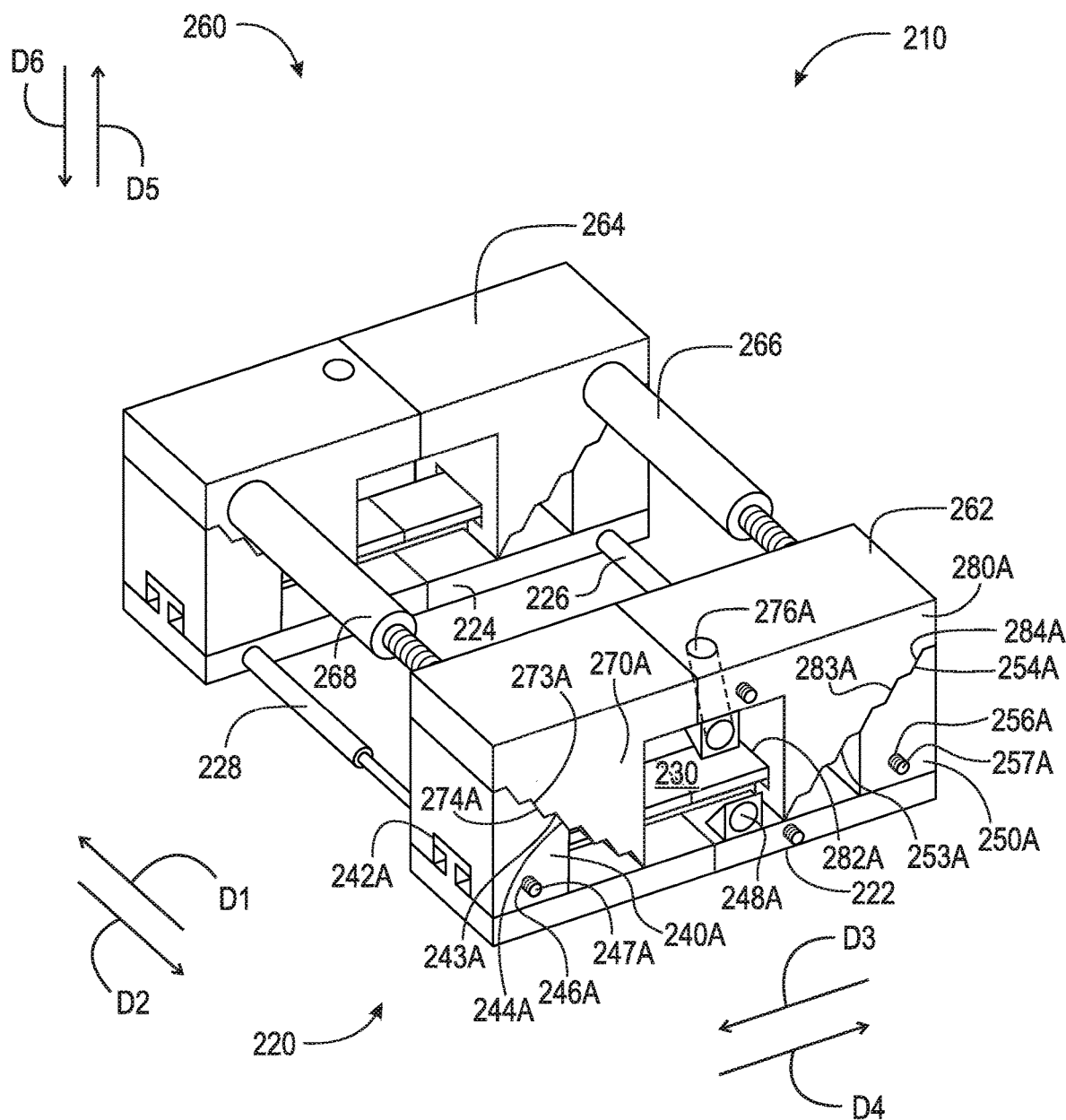
FIG. 13 is a front perspective view of an expandable intervertebral fusion implant, in a fully collapsed state.
Figure 14:
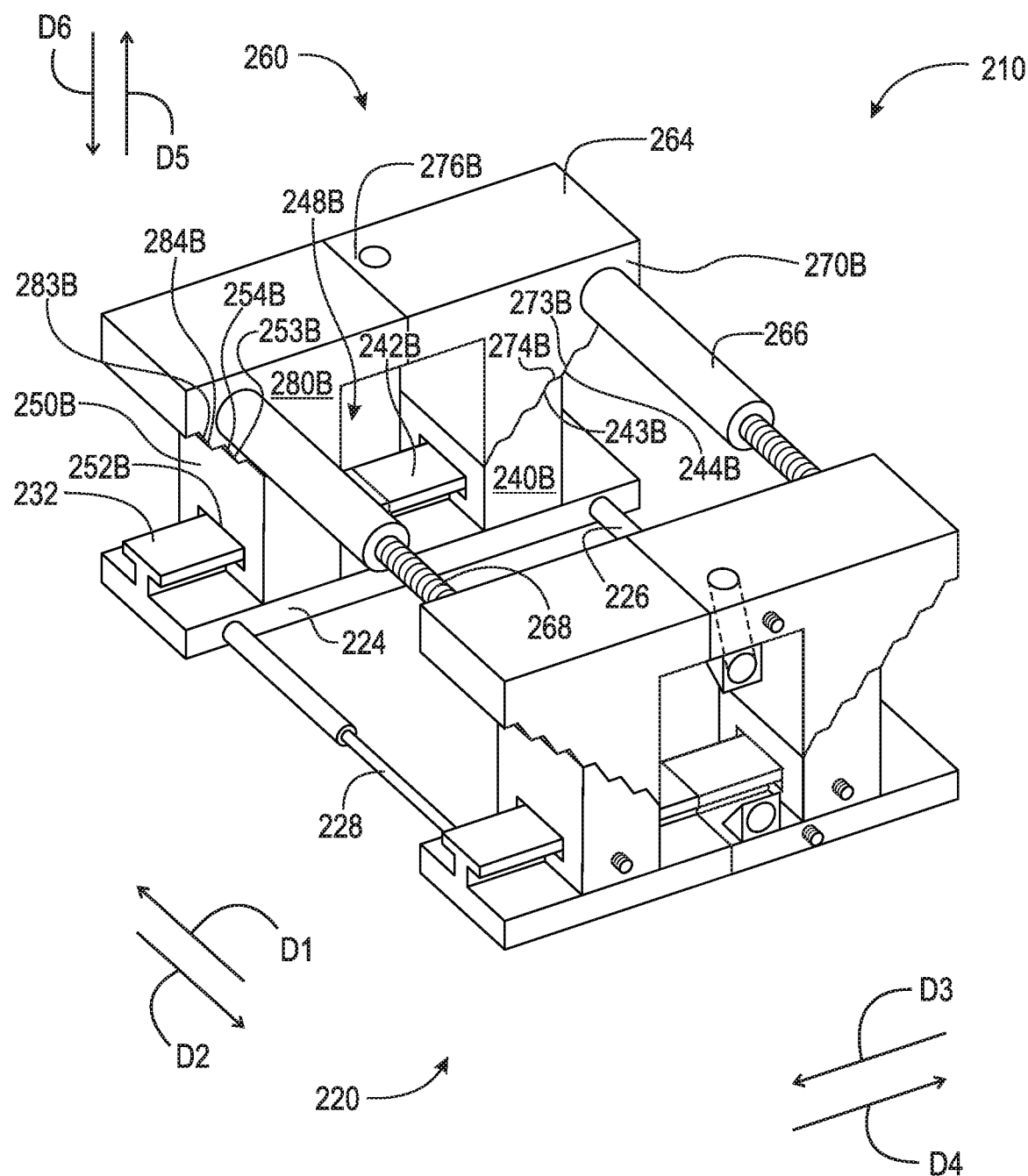
FIG. 14 is a front perspective view of the expandable intervertebral fusion implant shown in FIG. 13, in an expanded state; and, FIG. 15 is an anterior perspective view of a spinal column including the expandable intervertebral fusion implant shown in FIG. 7.

FIG. 13 is a front perspective view of expandable intervertebral fusion implant 210, in a fully collapsed state. FIG. 14 is a front perspective view of expandable intervertebral fusion implant 210, in an expanded state. Expandable intervertebral fusion implant 210 generally comprises inferior component 220 and superior component 260. The following description should be read in view of FIGS. 13-14.

Inferior component 220 comprises plate 222, plate 224, cross-member 226, cross-member 228, wedges 240A-B, and wedges 250A-B. In some embodiments, inferior component 220 comprises only plate 222, wedge 240A, and wedge 250A.

Wedges 240A and 250A are slidably engaged with plate 222. In some embodiments, and as shown in the figures, plate 222 comprises rail 230, and wedges 240A and 250A are slidably connected to rail 230. In some embodiments, plate 222 is expandable, as was discussed above with respect to FIG. 12.

Wedge 240A comprises groove 242A and teeth 244A arranged on angled surface 243A. In the embodiment shown in FIGS. 13-14, wedge 240A decreases in height in direction D4 (i.e., surface 243A slopes downward in direction D4). Groove 242A is operatively arranged to engage rail 230. Wedge 240A is arranged to displace relative to plate 222 in direction D3 and direction D4. Teeth 244A are operatively arranged to engage teeth 274A of wedge 270A of superior component 260 to expand expandable intervertebral fusion implant 210 and lock it at a set height, as will be discussed in greater detail below. Wedge 240A further comprises hole 246A and locking member 247A. As shown, locking member 247A is a set screw which engages threaded hole 246A in order to fixedly secure wedge 240A to rail 230. It should be appreciated that any means suitable for fixedly securing wedge 240A to plate 222 may be used (e.g., a clamp, crimping the wedge about the rail to fixedly secure it thereto, adhesives, bolts, rivets, welding, soldering, etc.), and that the present disclosure should not be limited to just the use of a set screw.

Wedge 250A comprises groove 252A and teeth 254A arranged on angled surface 253A. In the embodiment shown in FIGS. 13-14, wedge 250A decreases in height in direction D3 (i.e., surface 253A slopes downward in direction D3). Groove 252A is operatively arranged to engage rail 230. Wedge 250A is arranged to displace relative to plate 222 in direction D3 and direction D4. Teeth 254A are operatively arranged to engage teeth 284A of wedge 280A of superior component 260 to expand expandable intervertebral fusion implant 210 and lock it at a set height, as will be discussed in greater detail below. Wedge 245A further comprises hole 256A and locking member 257A. As shown, locking member 257A is a set screw which engages threaded hole 256A in order to fixedly secure wedge 250A to rail 230. It should be appreciated that any means suitable for fixedly securing wedge 250A to plate 222 may be used (e.g., a clamp, crimping the wedge about the rail to fixedly secure it thereto, adhesives, bolts, rivets, welding, soldering, etc.), and that the present disclosure should not be limited to just the use of a set screw. Plate 222 may further comprise hole 248A for securing inferior component 220 to an adjacent vertebra with, for example, a bone screw. Hole 248A is arranged at an angle relative to plate 222, for example, generally in direction D6, and does not interfere with rail 230.

Wedges 240B and 250B are slidably engaged with plate 224. In some embodiments, and as shown in the figures, plate 224 comprises rail 232, and wedges 240B and 250B are slidably connected to rail 232. In some embodiments, plate 224 is expandable, as was discussed above with respect to FIG. 12.

Wedge 240B comprises groove 242B and teeth 244B arranged on angled surface 243B. In the embodiment shown in FIGS. 13-14, wedge 240B decreases in height in direction D3 (i.e., surface 243B slopes downward in direction D3). Groove 242B is operatively arranged to engage rail 232. Wedge 240B is arranged to displace relative to plate 224 in direction D3 and direction D4. Teeth 244B are operatively arranged to engage teeth 274B of wedge 270B of superior component 260 to expand expandable intervertebral fusion implant 210 and lock it at a set height, as will be discussed in greater detail below. Wedge 240B further comprises hole 246B and locking member 247B (not shown). Locking member 247B is a set screw which engages threaded hole 246B in order to fixedly secure wedge 240B to rail 230. It should be appreciated that any means suitable for fixedly securing wedge 240B to plate 222 may be used (e.g., a clamp, crimping the wedge about the rail to fixedly secure it thereto, adhesives, bolts, rivets, welding, soldering, etc.), and that the present disclosure should not be limited to just the use of a set screw.

Wedge 250B comprises groove 252B and teeth 254B arranged on angled surface 253B. In the embodiment shown in FIGS. 13-14, wedge 250B decreases in height in direction D4 (i.e., surface 253B slopes downward in direction D4). Groove 252B is operatively arranged to engage rail 232. Wedge 250B is arranged to displace relative to plate 222 in direction D3 and direction D4. Teeth 254B are operatively arranged to engage teeth 284B of wedge 280B of superior component 260 to expand expandable intervertebral fusion implant 210 and lock it at a set height, as will be discussed in greater detail below. Wedge 245B further comprises hole 256B and locking member 257B (not shown). Locking member 257B is a set screw which engages threaded hole 256B in order to fixedly secure wedge 250B to rail 232. It should be appreciated that any means suitable for fixedly securing wedge 250B to plate 222 may be used (e.g., a clamp, crimping the wedge about the rail to fixedly secure it thereto, adhesives, bolts, rivets, welding, soldering, etc.), and that the present disclosure should not be limited to just the use of a set screw. Plate 222 may further comprise hole 248B for securing inferior component 220 to an adjacent vertebra with, for example, a bone screw. Hole 248B is arranged at an angle relative to plate 222, for example, generally in direction D6, and does not interfere with rail 232.

Cross-members 226 and 228 connect plate 224 to plate 222. In some embodiments, cross-members 226 and 228 are telescoping cross-members and allow for expandable intervertebral fusion implant 210 to be expanded and collapsed. For example, cross-members may comprise an inner rod slidable within an outer rod. Plate 224 may be displaced relative to plate 222 in direction D1 to expand expandable intervertebral fusion implant 210, specifically inferior component 220, and direction D2 to collapse expandable intervertebral fusion implant 210, specifically inferior component 220. Cross-members 226 and 228 are fixed to respective ends, or proximate ends, of plates 222 and 224. It should be appreciated that cross-members 226 and 228 do not have to be fixed at the ends of plates 222 and 224, but rather can be fixed axially inward from the ends of plates 222 and 224. In some embodiments, inferior component 220 comprises one cross-member that connects plates 222 and 224. In some embodiments, inferior component 220 does not comprise any cross-members. In some embodiments, inferior component 220 comprises one or more cross-members connecting plates 222 and 224, for example, three cross-members. It should be appreciated that although the drawings depict cross-members 226 and 228 having a circular cross-sectional geometry, any geometry suitable for expandably or displaceably connecting plates 222 and 224 may be used, for example, square, rectangular, triangular, ellipsoidal, etc. In some embodiments, cross-members 226 and 228 may be locking telescoping cross-members, similar or equivalent to cross-members 266 and 268 discussed in greater detail below. Additionally, it should be appreciated that in some embodiments, cross-members 226 and 228 are not telescoping and connect plate 224 to plate 222 at a set distance. Cross-members 226 and 228 may include an inner rod and an outer rod, and may also include threading (or locking pins) as discussed above with respect to FIG. 11.

Superior component 260 comprises component 262, component 264, cross-member 266, cross-member 268, wedges 270A-B, and wedges 280A-B. In some embodiments, superior component 260 comprises only component 262, wedge 270A, and wedge 280A.

Wedges 270A and 280A are connected to component 222. Wedge 270A comprises channel 272A and teeth 274A arranged on angled surface 273A. In the embodiment shown in FIGS. 13-14, wedge 270A decreases in height in direction D3 (i.e., surface 273A slopes downward in direction D3). Channel 272A is operatively arranged to engage rail 230 in a fully collapsed position, as is shown in FIG. 13. Channel 272A allows superior component 260 to fully collapse with respect to inferior component 220 (i.e., such that wedges 270A and 280A and wedges 270B and 280B rest on plates 222 and 224, respectively). Angled surface 273A is operatively arranged to engage angled surface 243A to expand superior component 260 with respect to inferior component 220. Specifically, as wedge 240A is displaced in direction D4 relative to plate 222, angled surface 243A engages angled surface 273A to displace superior component 260 in direction D5 relative to inferior component 220. Teeth 274A are operatively arranged to engage teeth 244A to lock superior component 260 at a distance relative to inferior component 220. Specifically, teeth 274A engage teeth 244A to allow wedge 240A to displace in direction D4 relative to plate 222, and at the same time, if required, allow wedge 240A to displace in direction D3 relative to plate 222. Such arrangement allows expandable intervertebral fusion implant 210 to expand and collapse in a controlled fashion.

Wedge 280A comprises channel 282A and teeth 284A arranged on angled surface 283A. In the embodiment shown in FIGS. 13-14, wedge 280A decreases in height in direction D4 (i.e., surface 283A slopes downward in direction D4). Channel 282A is operatively arranged to engage rail 230 in a fully collapsed position, as is shown in FIG. 13. Channel 282A allows superior component 260 to fully collapse with respect to inferior component 220 (i.e., such that wedges 270A and 280A and wedges 270B and 280B rest on plates 222 and 224, respectively). Angled surface 283A is operatively arranged to engage angled surface 253A to expand superior component 260 with respect to inferior component 220. Specifically, as wedge 250A is displaced in direction D3 relative to plate 222, angled surface 253A engages angled surface 283A to displace superior component 260 in direction D5 relative to inferior component 220. Teeth 284A are operatively arranged to engage teeth 254A to lock superior component 260 at a distance relative to inferior component 220. Specifically, teeth 284A engage teeth 254A to allow wedge 250A to displace in direction D3 relative to plate 222, and at the same time, if required, allow wedge 250A to displace in direction D4 relative to plate 222. Such arrangement allows expandable intervertebral fusion implant 210 to expand and collapse in a controlled fashion. Component 262 may further comprise hole 276A for securing superior component 260 to an adjacent vertebra with, for example, a bone screw. Hole 276A is arranged at an angle relative to plate 222, for example, generally in direction D5.

Wedges 270B and 280B are connected to component 224. Wedge 270B comprises channel 272B and teeth 274B arranged on angled surface 273B. In the embodiment shown in FIGS. 13-14, wedge 270B decreases in height in direction D4 (i.e., surface 273B slopes downward in direction D4). Channel 272B is operatively arranged to engage rail 232 in a fully collapsed position, as is shown in FIG. 13. Channel 272B allows superior component 260 to fully collapse with respect to inferior component 220 (i.e., such that wedges 270A and 280A and wedges 270B and 280B rest on plates 222 and 224, respectively). Angled surface 273B is operatively arranged to engage angled surface 243B to expand superior component 260 with respect to inferior component 220. Specifically, as wedge 240B is displaced in direction D3 relative to plate 222, angled surface 243B engages angled surface 273B to displace superior component 260 in direction D5 relative to inferior component 220. Teeth 274B are operatively arranged to engage teeth 244B to lock superior component 260 at a distance relative to inferior component 220. Specifically, teeth 274B engage teeth 244B to allow wedge 240B to displace in direction D3 relative to plate 222, and at the same time, if required, allow wedge 240B to displace in direction D4 relative to plate 222. Such arrangement allows expandable intervertebral fusion implant 210 to expand and collapse in a controlled fashion.

Wedge 280B comprises channel 282B and teeth 284B arranged on angled surface 283B. In the embodiment shown in FIGS. 13-14, wedge 280B decreases in height in direction D3 (i.e., surface 283B slopes downward in direction D3). Channel 282B is operatively arranged to engage rail 232 in a fully collapsed position, as is shown in FIG. 13. Channel 282B allows superior component 260 to fully collapse with respect to inferior component 220 (i.e., such that wedges 270A and 280A and wedges 270B and 280B rest on plates 222 and 224, respectively). Angled surface 283B is operatively arranged to engage angled surface 253B to expand superior component 260 with respect to inferior component 220. Specifically, as wedge 250B is displaced in direction D4 relative to plate 224, angled surface 253B engages angled surface 283B to displace superior component 260 in direction D5 relative to inferior component 220. Teeth 284B are operatively arranged to engage teeth 254B to lock superior component 260 at a distance relative to inferior component 220. Specifically, teeth 284B engage teeth 254B to allow wedge 250B to displace in direction D4 relative to plate 222, and at the same time, if required, allow wedge 250B to displace in direction D3 relative to plate 222. Such arrangement allows expandable intervertebral fusion implant 210 to expand and collapse in a controlled fashion. Component 262 may further comprise hole 276A for securing superior component 260 to an adjacent vertebra with, for example, a bone screw. Hole 276A is arranged at an angle relative to plate 222, for example, generally in direction D5.

Cross-members 266 and 268 connect component 264 to component 262. In some embodiments, cross-members 266 and 268 are telescoping cross-members and allow for expandable intervertebral fusion implant 210 to be expanded and collapsed. For example, cross-members may comprise an inner rod displaceable (or slidable) within an outer rod. Component 264 may be displaced relative to component 262 in direction D1 to expand expandable intervertebral fusion implant 210, specifically superior component 260, and direction D2 to collapse expandable intervertebral fusion implant 210, specifically superior component 260. Cross-members 266 and 268 are fixed to respective ends, or proximate ends, of components 262 and 264. It should be appreciated that cross-members 266 and 268 do not have to be fixed at the ends of components 262 and 264, but rather can be fixed axially inward from the ends of components 262 and 264. In some embodiments, superior component 260 comprises one cross-member that connects components 262 and 264. In some embodiments, superior component 260 does not comprise any cross-members. In some embodiments, superior component 260 comprises one or more cross-members connecting components 262 and 264, for example, three cross-members. It should be appreciated that although the drawings depict cross-members 266 and 268 having a circular cross-sectional geometry, any geometry suitable for expand-ably or displaceably connecting components 262 and 264 may be used, for example, square, rectangular, triangular, ellipsoidal, etc. Additionally, it should be appreciated that in some embodiments, cross-members 266 and 268 are not telescoping and connect component 264 to component 262 at a set distance. In some embodiments, cross-members 266 and 268 may include an inner rod and an outer rod, and may also include locking pins. In some embodiments, cross-members 266 and 268 comprise an inner rod threadably engaged with an outer rod, as discussed above with respect to FIG. 11.

Figure 15:
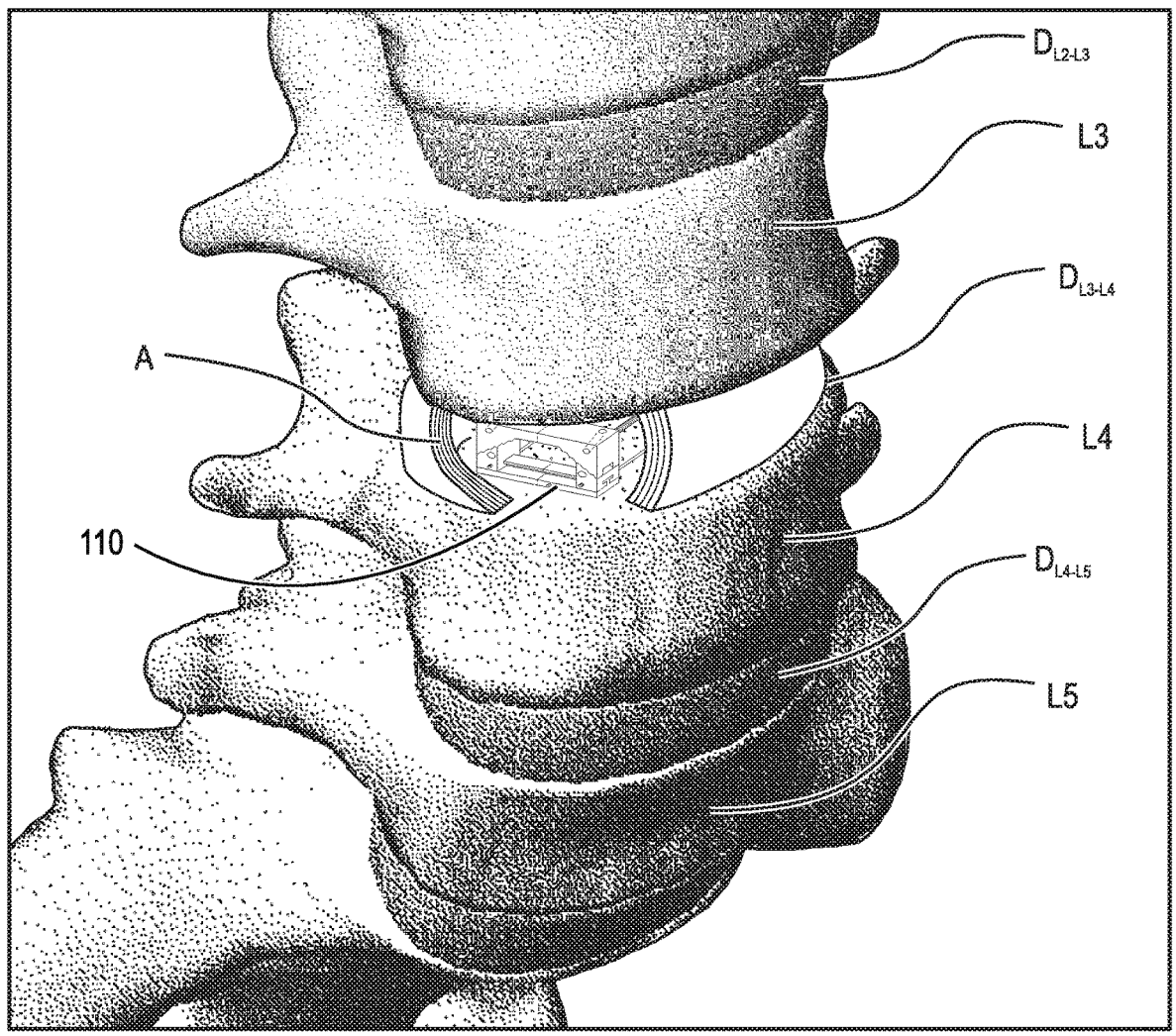

FIG. 15 is an anterior perspective view of a spinal column including expandable intervertebral fusion implant 110. Expandable intervertebral implant 110 is inserted into the spinal column between, for example, the L3 and L4 vertebrae, or where disc $D_{L3-L4}$ should be. Expandable intervertebral implant 110 is then vertically expanded until the desired height is reached. Expandable intervertebral implant 110 may be expanded in the anterior-posterior directions (i.e., directions D1 and D2) prior to insertion, or after insertion, as previously discussed (i.e., along telescoping cross-members). Expandable intervertebral implant 110 is then filled with fusion material and left in situ.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Spinal column
12 Ligament
C1-C7 Cervical vertebrae
T1-T12 Thoracic vertebrae
L1-L5 Lumbar vertebrae
S Sacrum
C Coccyx
$D_{L1-L2}$ Disc
$D_{L2-L3}$ Disc
$D_{L3-L4}$ Disc
$D_{L4-L5}$ Disc
F Facet
FJ Facet joint
SP Spinous process
TP Transverse process
IF Intervertebral foramen
NC Neural canal
A Annulus
N Nucleus
DH Disc space height
80 Runner
90 Channel
92 Opening
94 Side
96 Side
102 Threading
104 Threading
106 Hole
108 Screw
110 Expandable intervertebral fusion implant
120 Inferior component
122 Plate
122A Section 122B Section
123A Extension
123B Hole
124 Plate
126 Cross-member
126A Inner rod
126B Outer rod
128 Cross-member
128A Inner rod
128B Outer rod
130 Rail
132 Rail
140A Wedge
140B Wedge
142A Groove
142B Groove
143A Surface
143B Surface
144A Teeth
144B Teeth
146A Hole
146B Hole
147A Locking member (screw)
147B Locking member (screw)
148A Hole
148B Hole
150A Wedge
150B Wedge
152A Groove
152B Groove
153A Surface
153B Surface
154A Teeth
154B Teeth
156A Hole
156B Hole
157A Locking member (screw)
157B Locking member (screw)
158A Hole
158B Hole
160 Superior component
162 Component
164 Component
166 Cross-member
166A Inner rod
166B Outer rod
168 Cross-member
168A Inner rod
168B Outer rod
170A Wedge
170B Wedge
172A Channel
172B Channel
173A Surface
173B Surface
174A Teeth
174B Teeth
176A Hole
176B Hole
180A Wedge
180B Wedge
182A Channel
182B Channel
183A Surface
183B Surface
184A Teeth
184B Teeth 186A Hole
186B Hole
210 Expandable intervertebral fusion implant
220 Inferior component
222 Plate
224 Plate
226 Cross-member
226A Inner rod (not shown)
226B Outer rod (not shown)
228 Cross-member
228A Inner rod (not shown)
228B Outer rod (not shown)
230 Rail
232 Rail
240A Wedge
240B Wedge
242A Groove
242B Groove
243A Surface
243B Surface
244A Teeth
244B Teeth
246A Hole
246B Hole
247A Screw
247B Screw
248A Hole
248B Hole
250A Wedge
250B Wedge
252A Groove
252B Groove
253A Surface
253B Surface
254A Teeth
254B Teeth
256A Hole
256B Hole
257A Screw
257B Screw
260 Superior component
262 Component
264 Component
266 Cross-member
266A Inner rod (not shown)
266B Outer rod (not shown)
268 Cross-member
268A Inner rod (not shown)
268B Outer rod (not shown)
270A Wedge
270B Wedge
272A Channel
272B Channel
273A Surface
273B Surface
274A Teeth
274B Teeth
276A Hole
276B Hole
280A Wedge
280B Wedge
282A Channel
282B Channel
283A Surface
283B Surface
284A Teeth
284B Teeth D1 Direction
D2 Direction
D3 Direction
D4 Direction
D5 Direction
D6 Direction

What is claimed is:

1. An expandable intervertebral fusion implant, comprising:
   an inferior component, including:
      a plate; and,
      a first wedge slidably connected to the plate, the first wedge including a first surface comprising a first plurality of teeth; and,
   a superior component including a second wedge, the second wedge including a second surface comprising a second plurality of teeth;
   wherein:
      the first surface is operatively arranged to engage the second surface to displace the superior component relative to the inferior component;
      the second plurality of teeth are operatively arranged to engage the first plurality of teeth to maintain the expandable intervertebral fusion implant at a height and in a fully expanded position; and,
      in a fully collapsed position of the expandable intervertebral fusion implant, the first wedge and the second wedge are arranged entirely between the plate and the superior component.

2. The expandable intervertebral fusion implant as recited in claim 1, wherein the first plurality of teeth include a first plurality of stairs and the second plurality of teeth include a second plurality of stairs.

3. The expandable intervertebral fusion implant as recited in claim 2, wherein:
   each step in the first plurality of stairs includes a first tread arranged parallel to the plate and a first riser arranged at a first angle relative to the plate; and,
   each step in the second plurality of stairs includes a second tread arranged parallel to the first tread and a second riser arranged at a second angle relative to the plate.

4. The expandable intervertebral fusion implant as recited in claim 3, wherein the second riser is arranged parallel to the first riser.

5. The expandable intervertebral fusion implant as recited in claim 1, wherein the first wedge is operatively arranged to be locked to the plate.

6. The expandable intervertebral fusion implant as recited in claim 5, wherein the first wedge further comprises a screw operatively arranged to lock the first wedge with respect to the plate.

7. The expandable intervertebral fusion implant as recited in claim 1, wherein the plate comprises a rail, the first wedge being slidably engaged with the rail.

8. The expandable intervertebral fusion implant as recited in claim 1, wherein:
   the inferior component further comprises a third wedge having a third surface; and,
   the superior component further comprises a fourth wedge having a fourth surface;
   wherein the third surface is operatively arranged to engage the fourth surface to displace the superior component relative to the inferior component.

9. The expandable intervertebral fusion implant as recited in claim 8, wherein the third wedge is displaceable relative to the first wedge.

10. The expandable intervertebral fusion implant as recited in claim 8, wherein the fourth wedge is fixedly securable to the second wedge.

11. The expandable intervertebral fusion implant as recited in claim 8, wherein as the first wedge is displaced in a first direction relative to the plate, the superior component is displaced in a second direction relative to the inferior component.

12. The expandable intervertebral fusion implant as recited in claim 11, wherein as the third wedge is displaced in a third direction relative to the plate, the third direction being opposite the first direction, the superior component is displaced in the second direction relative to the inferior component.

13. The expandable intervertebral fusion implant as recited in claim 11, wherein the second direction is perpendicular to the first direction.

14. The expandable intervertebral fusion implant as recited in claim 1, wherein the plate is expandable.

15. The expandable intervertebral fusion implant as recited in claim 1, wherein the superior component is expandable.

16. An expandable intervertebral fusion implant, comprising:
   an inferior component, including:
      a first plate;
      a first wedge slidably connected to the first plate, the first wedge having a first surface;
      a second plate;
      a second wedge slidably connected to the second plate, the second wedge having a second surface; and,
      at least one first cross-member connecting the first and second plates; and,
   a superior component, including:
      a first component including a third wedge, the third wedge having a third surface;
      a second component including a fourth wedge, the fourth wedge having a fourth surface; and,
      at least one second cross-member connecting the first and second components;
   wherein:
      the first and second surfaces are operatively arranged to engage the third and fourth surfaces, respectively, to displace the superior component relative to the inferior component; and,
      in a fully collapsed position of the expandable intervertebral fusion implant, the first wedge and the third wedge are arranged entirely between the first plate and the first component.

17. The expandable intervertebral fusion implant as recited in claim 16, wherein at least one of the first surface and the second surface comprises a first plurality of teeth and at least one of the third surface and the fourth surface comprises a second plurality of teeth, the second plurality of teeth operatively arranged to engage the first plurality of teeth to maintain the expandable intervertebral fusion implant at a height.

18. The expandable intervertebral fusion implant as recited in claim 16, wherein at least one of the first wedge and the second wedge is operatively arranged to be locked to the first and/or second plates, respectively.

19. The expandable intervertebral fusion implant as recited in claim 16, wherein the first plate comprises a first rail, the first wedge being slidably engaged with the first rail.

20. The expandable intervertebral fusion implant as recited in claim 16, wherein:
   the inferior component further comprises:

a fifth wedge including a fifth surface, the fifth wedge slidably engaged with the first plate; and,
a sixth wedge including a sixth surface, the sixth wedge slidably engaged with the second plate; and,
the superior component further comprises:
a seventh wedge including a seventh surface, the seventh wedge connected to the first component; and,
an eighth wedge including an eighth surface, the eighth wedge connected to the second component;
wherein the fifth and sixth surfaces are operatively arranged to engage the seventh and eighth surfaces, respectively, to displace the superior component relative to the inferior component.

21. The expandable intervertebral fusion implant as recited in claim 20, wherein the first, second, fifth, and sixth wedges are displaceable relative to each other.

22. The expandable intervertebral fusion implant as recited in claim 20, wherein the third wedge is fixedly secured to the seventh wedge, and the fourth wedge is fixedly secured to the eighth wedge.

23. The expandable intervertebral fusion implant as recited in claim 20, wherein as the first wedge is displaced in a first direction relative to the first plate or the fifth wedge is displaced in a second direction, opposite the first direction, relative to the first plate, the superior component is displaced in a third direction relative to the inferior component.

24. The expandable intervertebral fusion implant as recited in claim 23, wherein as the second wedge is displaced in the first direction relative to the second plate or the sixth wedge is displaced in the second direction relative to the second plate, the superior component is displaced in the third direction.

25. The expandable intervertebral fusion implant as recited in claim 23, wherein the third direction is perpendicular to the first and second directions.

26. The expandable intervertebral fusion implant as recited in claim 16, wherein at least one of the first plate and the second plate is expandable.

27. The expandable intervertebral fusion implant as recited in claim 16, wherein at least one of the first and second cross-members are telescoping.

28. An expandable intervertebral fusion implant, comprising:
an inferior component, including:
a plate; and,
a first wedge slidably connected to the plate, the first wedge having a first surface; and,
a superior component including a second wedge, the second wedge having a second surface;
wherein:
the first wedge is operatively arranged to displace in a first direction from a middle of the plate to an end of the plate and the first surface is operatively arranged to engage the second surface to displace the superior component in a second direction away from the inferior component, the second direction being perpendicular to the first direction; and,
in a fully collapsed position of the expandable intervertebral fusion implant, the first wedge and the second wedge are arranged between the plate and the superior component.

* * * * *